US009815875B2

(12) United States Patent
Peters et al.

(10) Patent No.: US 9,815,875 B2
(45) Date of Patent: Nov. 14, 2017

(54) POSTSYNAPTICALLY TARGETED CHEMODENERVATION AGENTS AND THEIR METHODS OF USE

(75) Inventors: Lars Erik Peters, Lafayette, CO (US); Todd Lorenz, Corte Madera, CA (US)

(73) Assignee: MYOCEPT INC., Lafayette, CO (US)

( * ) Notice: Subject to any disclaimer, the term of this patent is extended or adjusted under 35 U.S.C. 154(b) by 1425 days.

(21) Appl. No.: 12/867,975

(22) PCT Filed: Feb. 19, 2009

(86) PCT No.: PCT/US2009/034578

§ 371 (c)(1), (2), (4) Date: Jan. 31, 2011

(87) PCT Pub. No.: WO2009/105585

PCT Pub. Date: Aug. 27, 2009

(65) Prior Publication Data

US 2011/0118190 A1 May 19, 2011

Related U.S. Application Data

(60) Provisional application No. 61/066,347, filed on Feb. 19, 2008.

(51) Int. Cl.

| | |
|---|---|
| ***A61K 39/395*** | (2006.01) |
| ***A61K 39/00*** | (2006.01) |
| ***C07K 16/00*** | (2006.01) |
| ***C07K 14/46*** | (2006.01) |

(52) U.S. Cl.

CPC .................................... *C07K 14/46* (2013.01)

(58) Field of Classification Search

CPC .... A61K 38/00; A61K 2800/57; A61K 38/16; C07K 14/43522; C07K 1/107; C07K 14/46; C07K 14/00; C07K 14/245; C07K 14/43572; C07K 14/811; C07K 2319/00; C07K 1/047; C40B 40/02

See application file for complete search history.

(56) References Cited

U.S. PATENT DOCUMENTS

| | | | | |
|---|---|---|---|---|
| 4,447,356 | A | 5/1984 | Olivera et al. | |
| 7,659,252 | B2 * | 2/2010 | Wen et al. | 514/1.1 |

FOREIGN PATENT DOCUMENTS

| | | |
|---|---|---|
| FR | 2762009 | 10/1998 |
| WO | 03002739 | 1/2003 |
| WO | 2006047900 | 5/2006 |
| WO | 2007035474 | 3/2007 |

OTHER PUBLICATIONS

Meng et al., Comparative Biochemistry and Physiology Part C, 2002. 132: 113-121.*
Servent et al., J. Biol. Chem. 1997, 272:24279-24286.*
Rosso et al. Eur. J. Biochem 1996, 238: 231-239.*
He et al. Toxicon 2004, 44: 295-303.*
Burgess et al. J of Cell Bio. 1990, 111:2129-2138.*
Bowie et al. Science, 1990, 247:1306-1310.*
Pawson et al. 2003, Science 300:445-452.*
Giraudat; et al."Identification of a cDNA clone coding for the acetylcholine binding subunit Torpedo marmorata acetylcholine receptor", Embo J (1982), 1(6):713-717.
Golovanov; et al. "Two-dimensional 1H-NMR study of the spatial structure of neurotoxin II from Naja naja oxiana", Eur J Biochem (May 1993), 213(3):1213-1223.
He; et al. "Cloning and purification of alpha-neurotoxins from king cobra (Ophiophagus hannah)", Toxicon (Sep. 2004), 4(3):295-303.
Lentz; et al. "Nicotine binding to native and substituted peptides comprising residues 188-207 of nicotinic acetylcholine receptor alpha1, alpha2, alpha3, alpha4, alpha5, and alpha7 subunits", Biochem Biophys Res Commun (Feb. 2000), 268(2):480-484.
Meng; et al. "A novel short neurotoxin, cobrotoxin c, from monocellate cobra (Naja kaouthia) venom: isolation and purification, primary and secondary structure determination, and tertiary structure modeling", Comp Biochem Physiol C Toxicol Pharmacol (May 2002), 132(1):113-121.
Zeng; et al. "The solution structure of the complex formed between alpha-bungarotoxin and an 18-mer cognate peptide derived from the alpha 1 subunit of the nicotinic acetylcholine receptor from Torpedo californica", J Biol Chem (Jun. 2001), 276(25):22930-22940.

* cited by examiner

*Primary Examiner* — Chang-Yu Wang

(57) ABSTRACT

Improved chemodenervation agents are provided comprising polypeptide α-neurotoxins having high binding specificity and selectivity for the human muscular α1 nAChR instead of the human neuronal α7 nAChR, along with pharmaceutical compositions and methods of use.

8 Claims, 1 Drawing Sheet

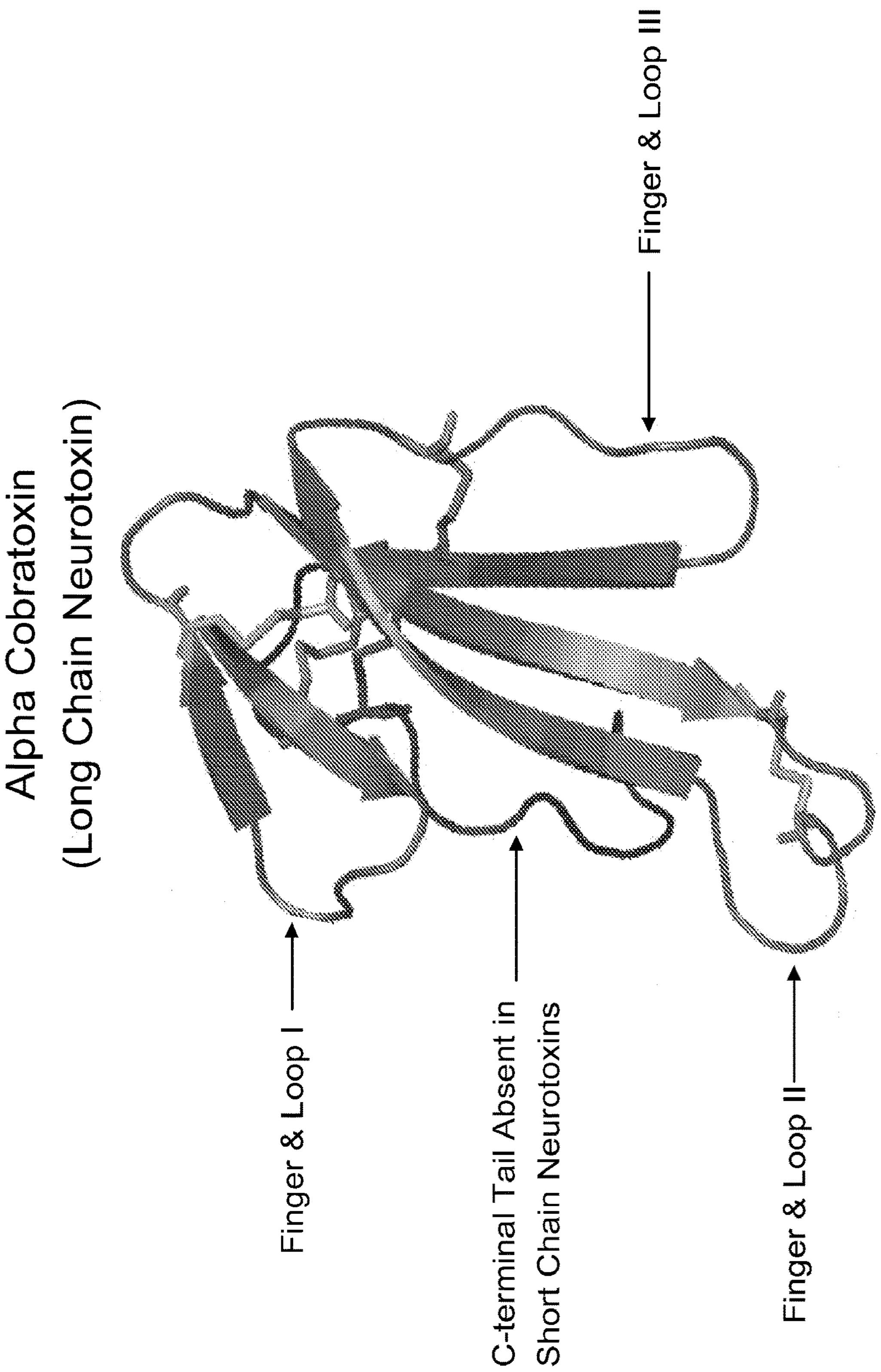
Alpha Cobratoxin
(Long Chain Neurotoxin)
Finger & Loop III
Finger & Loop I
C-terminal Tail Absent in
Short Chain Neurotoxins
Finger & Loop II

POSTSYNAPTICALLY TARGETED CHEMODENERVATION AGENTS AND THEIR METHODS OF USE

BACKGROUND

The treatment of neuromuscular disorders to date has almost universally focused on the development and delivery of therapeutic agents targeting the presynaptic (i.e. neuronal) side of the neuromuscular junction. The various *Clostridium* toxins in particular have been widely investigated in their native forms as chemodenervation agents. Unfortunately, however, due to the pleiotropic nature of neuronal function the presynaptic therapeutic approach espoused in the art can adversely impact smooth muscle signaling and inter-neuronal signaling in addition to the desired effect on skeletal muscle, thereby creating unwanted side effects and toxicities.

The botulinum toxins in particular demonstrate the problems inherent in presynaptic targeting for treatment of neuromuscular disorders. Over the last ten years commercial preparations of *Clostridium botulinum* toxins, including BoTox®, have found widespread use as chemodenervation agents for both aesthetic and clinical purposes. Notably, their use in treating symptoms of clinical neuromuscular disorders has recently come under more intense scrutiny by the FDA, due to leakage toxicity resulting in loss of critical smooth muscle cell function. Indeed, even some of the more prevalent toxicities associated with the aesthetic use of these molecules such as persistent dry mouth are again due to leakage of the toxin from the site of administration and inhibition of more distant smooth muscle cell function. In addition, many patients who initially respond to botulinum toxin therapy subsequently become non-responsive to the treatment. Accordingly, for many patients the botulinum injections fail to provide satisfactory long-term treatment of the condition. Nevertheless, despite these apparent drawbacks no alternative therapeutic strategies have been developed to date.

Other neurotoxins isolated from animal venoms are known to have postsynaptic mechanisms of action. For example, α-conopeptides from the venom of *Conus* marine snails are known to act postsynaptically on nAChRs. The class of snake venom proteins known as alpha-neurotoxins are also known to be competitive antagonists of nAChRs. α-Neurotoxins have a highly conserved fold, due primarily to four invariant disulfide bonds and are classified as either "short" with 60-62 residues and four disulfides, or "long" with 63-80 residues and a fifth disulfide. See Walkinshaw, M. D. et al. Proc. Natl. Acad. Sci. USA 77:2400-04 (1980). All of these toxins bind with high affinity to the muscular-type nAChR, and long chain toxins additionally recognize the alpha7 receptor of the neuronal-type nAChR with high affinity (Servent D. et al.; Eur J Pharmacol. 393(1-3):197-204 (2000).

Long chain α-neurotoxins modified for enhanced binding to the α7-subunit containing neuronal nAChR in particular have been suggested as optimal therapeutic agents for the specific inhibition of neurotransmission. See, e.g., U.S. Pat. No. 6,753,315. Unfortunately, however, this again follows the convention of presynaptic targeting and overlooks the problematic impact of such antagonists on interneuronal signaling and smooth muscle activity. Further, such antagonists can have a detrimental effect on the immune system due to the distribution of the α-7 nAChR. See, e.g., Wang et al., "Nicotinic acetylcholine receptor alpha 7 subunit is an essential regulator of inflammation," *Nature* 421:384-8 (2003).

α-conopeptides from the venom of *Conus* marine snails have been proposed for use in for muscle denervation and paralysis (Olivera et al. U.S. Pat. No. 4,447,356). However, the muscle paralysis achieved by α-conopeptides lasts only fifteen to twenty minutes, due to high dissociation rates and low biostability. For effective muscle denervation treatment a long-term paralytic effect lasting for several hours or days is desirable. Accordingly, α-conopeptides have not been developed as a viable alternative to conventional chemodenervation with botulinum toxin, and there remains a need for an alternative therapeutic approach to treating neuromuscular disorders that can effectively achieve skeletal muscle paralysis while reducing the adverse effects on neuronal and smooth muscle function that are observed with conventional therapeutic neurotoxins.

SUMMARY OF INVENTION

Contrary to the established convention in the art, the present inventors have developed agents that operate postsynaptically to effect immediate, temporary, and optionally partial skeletal muscle paralysis. This postsynaptic approach to chemodenervation offers many advantages over prior art presynaptic approaches (e.g., the use of botulinum toxin). First, the subject compositions have reduced toxicity as compared to presynaptically acting neurotoxins. The postsynaptically targeted chemodenervation polypeptides described herein act selectively on postsynaptic membranes at the skeletal neuromuscular junction. Selectivity for the muscle component of the neuromuscular junction and restriction to skeletal muscle greatly reduces the toxicity of the subject compositions as compared to presynaptically acting neurotoxins such as botulinum toxin. Secondly, unlike presynaptic approaches, postsynaptic chemodenervation as described herein does not involve a latency period between administration and effect. Postsynaptic chemodenervation as described herein is immediate. Thirdly, and relatedly, an effective dosage of postsynaptic chemodenervation polypeptide is immediately determinable. In contrast, the delayed effect of presynaptic chemodenervation makes it impossible to gauge effective dosage in real time. Fourthly, postsynaptic chemodenervation produces long-lasting but temporary paralysis. Postsynaptic chemodenervation has a duration of effect lying between the short-lasting α-conotoxins and the essentially permanently paralyzing neurotoxins, such as botulinum toxin. This is a highly desirable duration of effect, wherein prolonged paralysis can be achieved without frequent readministration, and temporary and partial paralysis are feasible. Further, the present invention provides a variety of postysynaptic chemodenervation agents having a range of potencies which broadens the duration range of paralysis achievable with this class of agents.

Accordingly, the present invention provides postsynaptic chemodenervation polypeptides, methods of making the same, and methods of using the same to treat neuromuscular disorders. The subject postsynaptic chemodenervation polypeptides include short chain α-neurotoxins, as well as long-chain α-neurotoxins that bind preferentially to human muscular nAchR instead of human neuronal, α7/4/3/2-containing nAChR. The subject polypeptides exhibit at least 100-fold higher affinity for human α1-subunit-containing, muscular nAchRs than for any of the human α7, α3, α4, α2-subunit-containing, neuronal nAChRs, more preferably at least 500-fold higher affinity, and still more preferably at least 1000-fold higher affinity. As described herein, the affinity of an α-neurotoxin for a particular human receptor can be expressed as the inverse equilibrium dissociation constant ($1/K_D$) measured in receptor binding assays with labeled toxin molecules.

Preferred neurotoxin molecules for use in the subject compositions and methods are further characterized by a slow equilibrium dissociation rate from the human muscular nAChR subtype. As described herein, the dissociation constant represents the molar concentration at which 50% of the neurotoxin exists as a free, dissociated molecule and 50% remains bound to the receptor.

The subject postsynaptic chemodenervation polypeptides find advantageous use in compositions and methods for nonpermanent and localized inhibition of muscle cell function, and for reducing neurotransmitter effects at neuromuscular junctions and thereby inducing the temporary paralysis of skeletal muscles. These effects are useful for the treatment of aberrant or undesired muscle contraction, inter alia in the cosmetic treatment of facial wrinkles, in strabismus, blepharospasm, various dystonias and other conditions having neuromuscular components, as well as in the transient paralysis of muscles in surgical settings requiring partial patient immobilization, such as various orthopedic interventions.

In some embodiments a composition of the invention consists essentially of a postsynaptic chemodenervation α-neurotoxin polypeptide having the binding constant characteristics as set forth herein. As used herein, "consisting essentially of" and grammatical equivalents thereof limit the scope of a claim to the specified materials and those that do not materially affect the basic and novel characteristic or characteristics of the claimed invention. For example, a composition consisting essentially of a polypeptide may be free of elements that materially impact the desired activity of the composition as a whole.

In one embodiment, the subject postsynaptic chemodenervation polypeptides are long chain α-neurotoxins. Long-chain α-neurotoxins generally comprise five disulfide bonds and invariably comprise 10 cysteine residues. (see Walkinshaw, supra, for reference). Exemplary native long-chain α-neurotoxin sequences are provided in Table 1 herein. In contrast, the long chain α-neurotoxin molecules employed in the present invention have only four disulfide bonds and are missing the typical disulfide bond at the tip of loop II (finger II). In one embodiment, isolated native long-chain α-neurotoxin molecules naturally lacking a fifth disulfide are employed as chemodenervation agents in accordance with the present teachings, examples of which are provided in Table 2 herein. In alternative embodiments, native long-chain α-neurotoxins having a fifth disulfide bond between the fourth and fifth cysteine residues from the N-terminus are modified to eliminate the bond. As shown in FIG. 1, the invariable four disulfide bonds in long-chain α-neurotoxins produce a beta strand three finger fold with a fifth disulfide bond formed at the tip of the second loop, which is either missing or eliminated in accordance with the teachings of the present invention.

In one embodiment, the subject postsynaptic chemodenervation polypeptides are long-chain α-neurotoxins wherein at least one of the fourth and/or fifth cysteine residues as counted from the N-terminus is replaced with an amino acid other than cysteine, preferably with an amino acid selected from the group consisting of methionine, valine, leucine, isoleucine, arginine, lysine, asparagine, glutamine, phenylalanine, tyrosine, tryptophan, more preferably with an amino acid selected from the group comprising serine, alanine, threonine and glycine.

In one embodiment, the subject postsynaptic chemodenervation polypeptides are short-chain α-neurotoxins, and more preferably recombinant short-chain α-neurotoxins expressed from suitable host/vector systems and purified as a homogeneous, single toxin composition. Short-chain α-neurotoxins comprise four disulfide bonds and invariably comprise 8 cysteine residues. (see Walkinshaw, supra, for reference). Exemplary native short-chain α-neurotoxin sequences are provided in Table 3 herein.

Preferred long chain and short chain α-neurotoxin molecules that can be isolated and/or modified in accordance with the present teachings include α-neurotoxins from snakes of the order elapidae, preferably from elapidae snakes belonging to the genii of *Naja, Dendroaspis, Pseudonaja, Ophiophaghus, Bungarus, Laticauda, Austrelaps, Lapemis, Pseudechis, Notechis, Oxyuranus, Tropidechis, Acanthophis, Aspidelaps, Astrotia* and *Demansia*, more preferably from *Naja kaouthia, Naja naja, Naja sputatrix, Naja haje haje, Naja oxiana, Naja nivea, Naja melanoleuca, Ophiophagus Hannah, Pseudonaja textiles, Dendroaspis viridis, Dendroaspis jamesoni, Dendroaspis viridis, Dendroaspis polylepis, Acanthophis antarcticus, Aspidelaps scutatus, Astrotia stokesiim, Austrelaps superbus, Bungarus candidus, Boulengerina annulata, Bungarus flaviceps, Bungarus multicinctus, Bungarus multicinctus, Demansia vestigiata, Laticauda laticaudata, Laticauda colubrine, Lapemis hardwickii, Laticauda semifasciata, Notechis scutatus, Oxyuranus scutellatus, Oxyuranus microlepidotus, Pseudechis australis*, and *Tropidechis carinatus*.

The α-neurotoxins described herein can be produced by any number of well-known techniques including, e.g., post-translational, limited cysteine reduction of isolated native α-neurotoxins, followed by stable chemical modification of the reduced cysteine residues; or genetic engineering of native nucleic acid sequences coupled with recombinant production, and/or chemical synthesis of the corresponding modified α-neurotoxin amino acid sequences.

In preferred embodiments, the subject postsynaptic chemodenervation polypeptides are provided as homogeneous compositions of a single α-neurotoxin species, or as a defined mixture of two or more α-neurotoxin species the sequences and activities of which are known. Recombinant α-neurotoxins are particularly preferred, produced by recombinant expression in a suitable host/vector system and purified to homogeneity. Recombinant α-neurotoxins can be expressed from cDNA cloned into an expression plasmid vector and cDNAs of individual α-neurotoxin molecules can be cloned from venom gland total RNA or mRNA preparations, using standard techniques that are well known in the art.

In one aspect, the invention provides methods of using the subject postsynaptic chemodenervation polypeptides for localized inhibition of skeletal muscle function, and for reducing neurotransmitter effects at neuromuscular junctions. In one embodiment, methods of transiently paralyzing a desired muscle or group of muscles in conjunction with surgical procedures is provided. The methods include administering to a muscle or group of muscles attendant to a surgical procedure a postsynaptic chemodenervation polypeptide in an amount effective to immobilize the muscle or group of muscles for the desired period, e.g., the duration of the surgical procedure, a portion thereof, or extending beyond the surgical procedure. The subject polypeptides significantly expand the surgeon's capabilities to effectuate tissue and bone repair without the need for prolonged and/or general anesthesia.

According to another aspect of the invention, methods of enhancing relaxation or slackening of cutaneous tissue are provided. The methods include locally administering to a cutaneous tissue a postsynaptic chemodenervation polypeptide according to the present invention in an amount effective to enhance denervation of skeletal muscle or a group of skeletal muscles present subcutaneous to the cutaneous tissue to enhance relaxation or slackening of the cutaneous tissue. In some embodiments, the polypeptide is administered subcutaneously. In other embodiments, the polypeptide is administered intramuscularly or transdermally. Preferably the relaxation or slackening of the cutaneous tissue results in lessening of wrinkles or fine lines of the skin.

In some embodiments the methods further include co-administering an anti-wrinkle agent selected from the group consisting of hydroxy acids and retinoids. In preferred embodiments the hydroxy acid is selected from the group consisting of α-hydroxy acids and β-hydroxy acids, which can be linear, branched or cyclic and saturated or unsaturated and the retinoid is selected from the group consisting of retinoic acid, retinol, retinol esters, hylauronic acid and/or collagen.

According to another aspect of the invention, methods of treating spasm or involuntary contraction in a muscle or a group of muscles in a subject are provided. The methods include administering to a muscle or a group of muscles in a subject in need of such treatment a postsynaptic chemodenervation polypeptide in an amount effective to inhibit spasm or involuntary contraction in the muscle or the group of muscles of the subject.

In some embodiments the subject in need of such treatment has blepharospasm, strabismus, spasmodic torticollis, focal dystonia, jaw dystonia, occupational dystonia, corneal ulceration (protective ptosis), spasmodic dysphonia (laryngeal dystonia), or facial dyskinesis such as Meige syndrome, hemifacial spasm, aberrant regeneration of facial nerves, or apraxia of eyelid opening.

In one aspect, the invention provides pharmaceutical compositions comprising postsynaptically targeted chemodenervation polypeptides and a pharmaceutically acceptable carrier.

In one aspect, methods for producing a medicament useful for the treatment of a neuromuscular disorder are provided.

These and other aspects of the invention, as well as various advantages and utilities, will be more apparent with reference to the detailed description of the preferred embodiments.

BRIEF DESCRIPTION OF THE DRAWINGS

FIG. 1 illustrates the beta strand three finger fold and five disulfide bonds commonly found in long chain α-neurotoxins, with the fifth disulfide shown at the tip of the second finger and loop.

DETAILED DESCRIPTION

As detailed herein, the present inventors have determined that postsynaptically targeted chemodenervation polypeptides are superior chemodenervation agents in comparison with prior art presynaptically acting neurotoxins. The subject postsynaptic chemodenervation polypeptides find advantageous use in compositions and methods for localized inhibition of muscle cell function, and for reducing neurotransmitter effects at neuromuscular junctions and thereby inducing the paralysis of skeletal muscles. These effects, referred to herein as "chemodenervation", are useful for the treatment of aberrant or unwanted muscle contraction, inter alia in the cosmetic treatment of facial wrinkles, in strabismus, blepharospasm, various dystonias and other conditions having neuromuscular components, as well as in the transient paralysis of muscles in surgical settings requiring partial patient immobilization, such as various orthopedic interventions.

Postsynaptic Chemodenervation Polypeptides

The subject postsynaptic chemodenervation polypeptides have at least 100-fold higher affinity for α1-subunit containing nAChRs than for α7-subunit nAChRs, more preferably at least 500-fold higher affinity, and still more preferably at least 1000-fold higher affinity.

The subject postsynaptically targeted chemodenervation polypeptides preferably have an equilibrium dissociation constant ($K_D$) of less than $1 \times 10^{-8}$ M, more preferably less than $1 \times 10^{-9}$ M, more preferably less than $1 \times 10^{-10}$ M, and in some embodiments less than $1 \times 10^{-11}$ M.

In one embodiment, the subject postsynaptically targeted chemodenervation polypeptides preferably have an equilibrium rate of dissociation ($k_{off}$) less than less than $1 \times 10^{-3}$ min$^{-1}$, more preferably less than $1 \times 10^{-4}$ min$^{-1}$, more preferably less than $1 \times 10^{-5}$ min$^{-1}$, and in some embodiments less than $1 \times 10^{-6}$ min$^{-1}$.

In one embodiment, the subject postsynaptically targeted chemodenervation polypeptides preferably have a equilibrium rate constant of association ($k_{on}$) more than is $1 \times 10^{6}$ M$^{-1}$ min$^{-1}$, more preferably more than $1 \times 10^{7}$ M$^{-1}$ min$^{-1}$.

In one embodiment, isolated short chain α-neurotoxins are provided as postsynaptically targeted chemodenervation polypeptides. In another embodiment, isolated native long chain α-neurotoxins lacking the typical disulfide bond in the finger tip portion of loop 2 are provided as postsynaptically targeted chemodenervation polypeptides. In another embodiment, isolated modified long chain α-neurotoxins lacking the typical disulfide bond in the finger tip portion of loop 2 are provided as postsynaptically targeted chemodenervation polypeptides.

Thus the invention embraces isolated short chain α-neurotoxins, isolated native long chain α-neurotoxins lacking the typical disulfide bond in the finger tip portion of loop 2 (i.e., the disulfide bond normally occurring between the fourth and fifth cysteine residues from the N-terminus of the polypeptide), and isolated modified long chain α-neurotoxins lacking the typical disulfide bond in the finger tip portion of loop 2. In preferred embodiments, the subject α-neurotoxins are recombinant.

As used herein, a "functional variant", "variant" or "modification" of a native long-chain α-neurotoxin molecule (i.e., a "modified long-chain α-neurotoxin") is a molecule containing at least 63 amino acid residues and having only four disulfide bonds in comparison with five disulfide bonds in the corresponding native polypeptide. As used herein, "native" long-chain α-neurotoxin molecules are the wild-type molecules found in the venom of various snake species, including those disclosed in Table 2 for which the complete amino acid sequences are shown. Short chain α-neurotoxins naturally lack a fifth disulfide bond. Modified short chain α-neurotoxins (e.g., variants comprising conservative amino acid substitutions) wherein the variant maintains its capacity to selectively bind to the α-1 nAChR, preferably with an affinity comparable to native short chain α-neurotoxin, are also embraced by the invention.

DNA clones encoding native long-chain α-neurotoxins and short-chain α-neurotoxins can be readily obtained by one of ordinary skill in the art using published sequence information and employing conventional recombinant DNA techniques, such as gene synthesis, RNA isolation, reverse transcription to cDNA from isolated total RNA or mRNA coupled with amplification of individual α-neurotoxin coding-sequences from cDNA pool by polymerase chain reaction (PCR) with neurotoxin-specific primers designed after published sequence information.

The present invention recognizes for the first time that neurotoxins with postsynaptic mechanisms of action provide superior chemodenervation agents for use in the paralysis of skeletal muscles. The subject agents offer several advantages over prior art presynaptically acting agents. These include lower toxicity and fewer side effects, lack of latency for the paralysis effect, immediately determinable effective dosage, and a temporary but long-lasting paralysis. Further, a variety of postsynaptically targeted chemodenervation polypeptides having a range of potencies are provided, which broadens the range of paralysis duration achievable with this class of agents.

"Affinity" as used herein is expressed as the inverse equilibrium dissociation constant of the individual α-neurotoxin with the targeted nAChR. In one embodiment, a long chain α-neurotoxin employed in the subject compositions and methods exhibits an at least 10-fold lower equilibrium dissociation constant from the human muscular nAChR than typical short-chain α-neurotoxins, such as erabutoxin b, or α-conotoxins, preferably an at least 100-fold lower equilibrium dissociation constant and, more preferably, an at least 500-fold lower lower equilibrium dissociation constant.

In one embodiment, the postsynaptically targeted chemodenervation polypeptides employed in the subject compositions and methods exhibit in vivo a muscular denervation effect lasting for at least 2, 4 or 6 hours, more preferably for at least 8, 12 or 24 hours, preferably for at least 48 hours, more preferably for at least 3-7 days.

The subject compositions comprise isolated subject postsynaptically targeted chemodenervation polypeptides. As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

Modified α-Neurotoxins

In one embodiment, the postsynaptically targeted chemodenervation polypeptide of the invention is a modified α-neurotoxin molecule.

Modifications to the α-neurotoxin molecules can be made to a nucleic acid which encodes the polypeptide, and can include deletions, point mutations, truncations, amino acid substitutions and additions of amino acids. Alternatively, modifications can be made directly to the polypeptide itself, such as by irreversible, chemical reduction of the cysteines in a disulfide bond, cleavage, addition of a linker molecule, addition of a detectable moiety, such as biotin, addition of a fatty acid, pegylation, substitution of one amino acid for another and the like. The α-neurotoxins of the present invention can be composed of amino acids joined to each other by peptide bonds or modified peptide bonds, i.e., peptide isosteres, and may contain amino acids other than the 20 gene-encoded amino acids. The α-neurotoxins may be modified by either natural processes, such as posttranslational processing, or by chemical modification techniques which are well known in the art. Such modifications are well described in basic texts and in more detailed monographs, as well as in a voluminous research literature.

Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

Functional variants of native and modified α-neurotoxin molecules include fragments of the polypeptide molecules. A fragment, as used herein, is an α-neurotoxin molecule lacking one or more amino acids of a native α-neurotoxin amino acid sequence. Fragments may have amino acid(s) removed from one or both ends of the α-neurotoxin molecule, or in the internal sequence of the molecule, and combinations of these. The fragments employed in this invention must retain at least a substantial portion of the muscular nAchR binding activity of the full-length α-neurotoxin molecule from which the fragments were derived (native or modified long-chain α-neurotoxin molecules). It is within the skill of one of ordinary skill in the art to test the fragments to determine the binding activity of the fragment. Exemplary methods for determining nAchR binding are provided below in the Examples, along with preferred cell lines for use in such methods.

Where the native long-chain α-neurotoxin sequence includes a fifth disulfide bond formed between the fourth and fifth cysteine residues from the N-terminus of the polypeptide, preferred modifications will result in the permanent elimination of that bond to enhance selectivity for the human, muscular nAChR. In one embodiment, chemical reduction with thiol-reactive alkylation reagents is employed to eliminate permanently the fifth disulfide bond in an isolated native long-chain α-neurotoxin. In an alternative and preferred embodiment, genetic engineering techniques are employed to alter the coding sequence of at least one of the fourth or fifth cysteines downstream from the N-terminus of the native sequence such that the resulting polypeptide will form only four disulfide bonds. Particularly preferred variants will have at least one of the fourth or fifth cysteines replaced with an amino acid other than cysteine, preferably with an amino acid selected from the group consisting of valine, leucine, isoleucine, arginine, lysine, asparagine, glutamine, phenylalanine, tyrosine, tryptophane, more preferably with an amino acid selected from the group comprising serine, alanine, threonine, methionine and glycine.

If the modified α-neurotoxin molecules include additional amino acid substitutions without a change in binding specificity, then conservative amino acid substitutions typically will be preferred, i.e., substitutions which retain a property of the original amino acid such as charge, hydrophobicity, polarity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Such conservative substitutions may also be made in the derivation of short chain α-neurotoxin variants.

The invention also includes the use of nucleic acid sequences which include alternative codons that encode the same amino acid residues of the α-neurotoxin molecules. Leucine residues, for example, can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues include: GUA, GUC, GUG and GUU (valine codons); GGU, GGA, GGG, GGC (glycine codons); UAC and UAU (tyrosine codons). Other amino acid residues may be encoded similarly by multiple nucleotide sequences. Thus, the invention embraces degenerate nucleic acids that differ from the nucleic acids encoding native α-neurotoxin molecules in codon sequence due to the degeneracy of the genetic code.

It will also be understood that the invention embraces the use of the sequences in expression vectors, as well as to transfect host cells and cell lines, be these prokaryotic (e.g., *Escherichia coli*), or eukaryotic (e.g., yeast expression systems such as *Pichia pastoris* and *Saccharomyces cerevisiae*, CHO cells, COS cells, and recombinant baculovirus expression in insect cells). The expression vectors require that the pertinent sequence, i.e., those described supra, be operably linked to a promoter.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids, bacteria genomes and virus genomes. A cloning vector is one which is able to replicate in a host cell or be replicated after its integration into the genome of a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Preferably, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (RNA) encoding a postsynaptic chemodenervation polypeptide molecule. That heterologous DNA (RNA) is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences.

The expression vector is selected to be compatible with the host organism. A wide variety of host/expression vector combinations can be employed for expressing the postsynaptically targeted chemodenervation polypeptide encoding DNA. Numerous host cell lines, expression vectors, and expression vector components are commercially available. Compatible host/expression vector combinations can be readily selected by those of skill in the art. In a preferred embodiment of the invention, the host organism is *Pichea pastoris* and the expression vector is one of the pPIC series vectors (Invitrogen; Carlsbad, Calif.; see also Examples section). In another embodiment of the invention, the host organism is *Escherichia coli* and the expression vector is one of the pET series vectors (Novagen; Madison, Wis.; see also Examples section), in particular, pET-vectors providing a secretion signal pre-sequences for export of the recombinant α-neurotoxin into the periplasmatic space.

The preferred method for obtaining the postsynaptic chemodenervation polypeptides for use in this invention is by recombinant production, which involves genetic transformation of a host cell with a recombinant DNA vector encoding a postsynaptic chemodenervation polypeptide according to the present teachings, expression of the recombinant DNA in the transformed host cell, and collection and purification of the polypeptide. Preferably, the host organism is unicellular. More preferably, the host organism is a yeast, particularly *Pichia pastoris*, or bacteria, particularly *E. coli*.

Although native α-neurotoxins can be obtained directly by purification from snake venoms, the amount of an individual α-neurotoxin obtainable from a single specimen is rather small. In addition, the purification of individual α-neurotoxins to homogeneity from venoms is very costly and laborious. Attempts to purify significant quantities of individual neurotoxins from snake venoms are further hampered by the fact that any snake venom contains a myriad of three finger toxin polypeptides with similar physicochemical properties, which are difficult to separate from each other. This entails likelihood of cross-contaminations by similar three-finger neurotoxins. Due to the wide spectrum of toxic effects exerted by different three finger toxins, such cross-contamination can lead to unpredictable and potentially severe side effects. Accordingly, the subject postsynaptic chemodenervation polypeptides are preferably provided as a homogenous composition of a single α-neurotoxin molecule, or a defined mixture of two or more α-neurotoxin species, the sequences and activities of which are known and characterized.

Chemical synthesis using solid-phase strategy is another alternative to obtain substantially pure postsynaptically targeted chemodenervation polypeptides, which has been successfully demonstrated by Mourier G. et al. (Protein Eng. 2000 March; 13(3):217-25). Due to size of the inventive polypeptides ranging from 60-80 amino acids, however, this method is less preferred for commercial production.

The desired substantially pure postsynaptically targeted chemodenervation polypeptides are best practically obtained in commercially valuable amounts by recombinant expression in a suitable host organism followed by chromatographic purification. The postsynaptically targeted chemodenervation polypeptides can be produced by recombinant DNA techniques well known in the art. Such techniques are described by Sambrook et al. (1989). Nucleic acid sequences coding for the α-neurotoxin polypeptides can be isolated and cloned using conventional techniques. Alternatively, nucleic acid sequences coding for the α-neurotoxin polypeptides can be synthesized on the basis of the polypeptide amino acid sequences and the known degeneracy of the genetic code. The nucleic acids for the polypeptides can be designed to achieve maximal expression in a given host system. The polypeptides produced in this manner are isolated, reduced if necessary, and oxidized to form the four desired disulfide bonds, as detailed herein. A variety of commercially available host-vector systems optimized for correct folding and disulfide formation in vivo, which are well known to anyone skilled in the art, can be employed for that purpose. Lyukmanova E. N., et al. (J Biol Chem. 2007 Aug. 24; 282(34):24784-91.), Peng L. S. et al. (Toxicon. 2003 December; 42(7):753-61) and Wang Y. et al. (J Biotechnol. 2002 Apr. 11; 94(3):235-44), included herein as a reference, have successfully demonstrated the high-yield expression of biologically active long chain and short chain α-neurotoxins molecules in *Escherichia coli* and *Pichia pastoris*.

One method of forming disulfide bonds in the α-neurotoxins of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent α-neurotoxin molecule. However, because of the dilution resulting from the presence of other fractions of less biopotency, a somewhat higher dosage may be required.

Peptide analogs and peptide mimetics which are specific for muscular nAChR may also be prepared on the basis of the teachings disclosed herein using conventional drug modeling, drug design and combinatorial chemistry. Suitable techniques include, but are not limited to those described in U.S. Pat. No. 5,571,698, WO 95/21193, Ecker and Cook (Bio/Technology 13:351-360 (1995), Persidis and Persidis (Bio/Technology 15:1035-1036 (1997)), Johnson et al. ("Peptide Turn Mimetics" in Biotechnology and Pharmacy, Pezzato et al., eds., Chapman and Hall, New York (1993)), Sun and Cohen (Gene 137:127-132 (1993)) and the references cited therein. The development of peptide analogs and peptide mimetics are prepared using commercially available drug design software, including those set forth in the Persidis and Persidis reference. These peptide analogs and peptide mimetics have the same activities as the α-neurotoxins described herein and in the published literature. Peptide analogs and derivatives can be made in accordance with conventional techniques. Suitable techniques for peptide synthesis is described in U.S. Pat. No. 5,514,774, as well as the references cited therein. Peptide mimetics are similarly synthesized by conventional techniques.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

Modified short chain α-neurotoxins wherein the variant maintains its capacity to selectively bind to the α-1 nAChR, preferably with an affinity comparable to native short chain α-neurotoxin, are also embraced by the invention. Such variants comprising conservative amino acid substitutions are preferred.

Methods of Use

The subject postsynaptically targeted chemodenervation polypeptides find advantageous use in compositions and methods for localized inhibition of muscle cell function, and for reducing neurotransmitter effects at neuromuscular junctions and thereby inducing the paralysis of skeletal muscles. These effects, referred to herein as "chemodenervation", are useful for the treatment of aberrant muscle contraction, inter alia in the cosmetic treatment of facial wrinkles, in strabismus, blepharospasm, various dystonias and other conditions having neuromuscular components, as well as in the transient paralysis of muscles in surgical settings requiring partial patient immobilization, such as various orthopedic interventions.

In one embodiment, methods of treating spasm or involuntary contraction in a muscle or a group of muscles in a subject are provided. The methods include administering to a muscle or a group of muscles in a subject in need of such treatment a subject postsynaptically targeted chemodenervation polypeptide in an amount effective to inhibit spasm or involuntary contraction in the muscle or the group of muscles of the subject.

Topical administration of the subject postsynaptically targeted chemodenervation polypeptides is highly desirable. Examples of disorders amenable to treatment by the topical administration of the compositions set forth herein include, and are not limited to, wrinkles, such as brow furrows, headaches, such as migraine, headache pain, cervical dystonia, focal hand dystonia, neurogenic inflammation, blepharospasm, strabismus, hemifacial spasm, eyelid disorder, cerebral palsy, focal spasticity, limb spasticity, tics, tremors, bruxism, anal fissure, fibromyalgia, dysphagia, lacrimation, and pain from muscle spasms. The topical administration of the subject postsynaptically targeted chemodenervation polypeptides reduces the pain experienced by the patient when the polypeptide is administered because the patient does not need to be stuck with a needle that activates sensory pain neurons below the skin. The compositions disclosed herein provide localized relief with the subject postsynaptically targeted chemodenervation polypeptides, without risking systemic administration of the same.

A number of other conditions in which induction of muscle paralysis is desirable include those disease states where botulinum toxin administration is currently being utilized. Examples of such disease states and methods of administration are described in detail in U.S. Pat. No. 5,298,019 to Borodic (decreasing spasm or involuntary contraction in a muscle or group of muscles of a patient induced by pathologic neural stimulation caused by cerebrospinal injury or stroke); U.S. Pat. No. 5,721,215 to Aoki et al. (treatment of neuromuscular disorders); U.S. Pat. No. 5,714,468 to Binder (reduction of migraine headache pain); U.S. Pat. No. 5,670,484 to Binder (treating skin lesions associated with a cutaneous cell-proliferative disorder); and other patents in the patent families of the foregoing, the contents of which are expressly incorporated herein by reference in their entirety.

The subject postsynaptically targeted chemodenervation polypeptides also can be used for treatment of cerebral palsy-related lower extremity spasticity (Koman et al., J. Pediatr. Orthop. 20(1):108-115, 2000), achalasia (Kolbasnik et al., Am. J. Gastroenterol. 94(12):3434-3439, 1999), pathologic lacrimation (Riemann et al., Ophthalmology 106 (12):2322-2324, 1999), vocal fold granulomas (Orloff et al., Otolaryngol. Head Neck Surg. 121(4):410-413, 1999), pancreas divisum and acute recurrent pancreatitis, (Wehrmann et al., Gastrointest. Endosc. 50(4):545-548, 1999), acute-onset esotropia (Dawson et al., Ophthalmology 106(9): 1727-1730, 1999), and other conditions, especially those which benefit from amelioration of aberrant muscle control.

The subject postsynaptically targeted chemodenervation polypeptides also can be used for cosmetic treatments, including alone (Carruthers et al., J. Am. Acad. Dermatol. 34(5 Pt 1):788-977, 1996; Frankel et al., Arch. Otolaryngol Head Neck Surg. 124(3):321-323, 1998), in combination with other anti-wrinkle agents useful in cosmetic skin treatment including, e.g., botulinum toxins, or in combined therapy with laser resurfacing and surgical procedure (Carruthers et al., Dermatol. Surg. 24(11):1244-7, 1998), and the like. As is known to one of ordinary skill in the art, anti-wrinkle agents can also include α-hydroxy acids and β-hydroxy acids, which can be linear, branched or cyclic and saturated or unsaturated, retinoids including retinoic acid, retinol and retinol esters, collagen and hyaluronic acid, and the agent described in U.S. Pat. No. 5,869,068.

Other indications may include scoliosis, for which *Botulinum* toxin A has been suggested. See U.S. Pat. No. 5,053, 005 to Borodic. More generally, all indications for which *Botulinum* toxin A has been suggested as a treatment to relax skeletal muscle are included among the present indications which are treatable by the subject postsynaptically targeted chemodenervation polypeptides.

For the treatment of strabismus with *Botulinum* toxin type A, see Elston, J. S., et al., British Journal of Ophthalmology, 1985, 69, 718-724 and 891-896. For the treatment of blepharospasm with *Botulinum* toxin type A, see Adenis, J. P., et al., J. Fr. Ophthalmol., 1990, 13 (5) at pages 259-264. For treating squint, see Elston, J. S., Eye, 1990, 4(4):VII. For treating spasmodic and oromandibular dystonia torticollis, see Jankovic et al., Neurology, 1987, 37, 616-623.

Spasmodic dysphonia has been treated with *Botulinum* toxin type A. See Blitzer et al., Ann. Otol. Rhino. Laryngol, 1985, 94, 591-594. Lingual dystonia was treated with *Botu-*

*linum* toxin type A according to Brin et al., Adv. Neurol. (1987) 50, 599-608. Finally, Cohen et al., Neurology (1987) 37 (Suppl. 1), 123-4, discloses the treatment of writers cramp with *Botulinum* toxin type A.

Methods of treatment according to the present invention comprise the administration of the subject postsynaptically targeted chemodenervation polypeptides to effectively cause chemodenervation and temporary muscle paralysis.

The subject postsynaptically targeted chemodenervation polypeptides are administered in effective amounts. An effective amount is a dosage of the subject polypeptide sufficient to provide a medically or cosmetically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with treating spasm or involuntary contraction in a muscle or a group of muscles in a subject, an effective amount is that amount which inhibits or reduces the spasm or involuntary contraction. Likewise, an effective amount for lessening the appearance of wrinkles or fine lines in the skin would be an amount sufficient to lessen or inhibit the muscular contractile tone of the group of muscles present subcutaneously under the wrinkled cutaneous surface so as to allow relaxation of the cutaneous surface and enhance its smoothness. Thus, it will be understood that the subject postsynaptically targeted chemodenervation polypeptides can be used to treat the above-noted conditions according to the preferred modes of administration described below. It is preferred generally that a maximum dose be used, that is, the highest safe dose according to sound medical judgment. Repeated administrations of small doses so as to reduce 'spillage' and therefore unnecessary effects in the non-targeted tissue may be preferred.

Advantageously, the subject postsynaptically targeted chemodenervation polypeptides lack a latency period between administration and paralysis. Accordingly, an effective dosage is immediately determinable. The administrator may initiate treatment with a first dosage and upon finding paralysis to be below the desired level may increase the dosage stepwise in order to achieve the desired level or extent of paralysis.

A subject, as used herein, refers to any mammal (preferably a human, and including a non-human primate, cow, horse, pig, sheep, goat, dog, cat or rodent) with a condition requiring inhibition of neuronal activity, leading to extended periods of paralysis (such as the conditions described above).

Cosmetic Wrinkle Reduction

Facial expression lines such as the transverse forehead lines or the nasolabial fold are created by attachments of projections of facial muscles into the dermis. Contraction of facial muscles generally is well known to produce the various characteristic forms of facial expressions such as smiling, grimacing, etc. In addition, exaggeration of facial lines also is associated with the aging process. The general principle of the application of the subject postsynaptically targeted chemodenervation polypeptides is to limit the tonic contractile state of facial muscles so as to reduce muscle tone and to improve or change the quality and characteristics of facial expression.

In a preferred embodiment, the transverse forehead lines may be reduced in intensity by injecting a quantity of subject postsynaptically targeted chemodenervation polypeptide with a diffusion field of approximately 5 to 10 mms in four injection sites at the superior border of the forehead and at a point approximately 15 mms superior to the brow. This is done symmetrically on both sides of the forehead. The glabellar lines (the frowning lines in the mid position of the forehead) may be targeted by treating the glabellar muscles with a quantity producing a field of denervation of 5 to 10 mms. The subject postsynaptically targeted chemodenervation polypeptide is injected 15 mms above the brow line in the mid position of the forehead. The nasal labial fold lines can be diminished in their intensity by treating the zygomatic major and minor muscles which emanate from the zygomatic arch and extend diagonally to the position of the nasal labial fold. An injection of subject polypeptide diffusing a distance of 5 to 10 mms over the superior border of these muscles will diminish this line effectively. Furthermore, the position of the lips can be controlled by injecting the zygomatic major and minor muscles. The protrusion of the upper lip can be reduced and even inverted by injection of these muscles. In addition, the protrusion of the lower lip can be reduced by injecting the mentalis muscle at doses producing a denervating field of 5 to 10 mms at the level of the chin approximately 15 mms inferior to the lower lips at a point of approximately 5 mms from the midline.

Alternatively, and advantageously as compared to botulinum toxins, transdermal systems can also be employed to delivery the subject postsynaptically targeted chemodenervation polypeptides to accomplish similar denervation fields as done by injection.

The methods may further include co-administering an anti-wrinkle agent selected from the group consisting of hydroxy acids and retinoids. In preferred embodiments the hydroxy acid is selected from the group consisting of α-hydroxy acids and β-hydroxy acids, which can be linear, branched or cyclic and saturated or unsaturated and the retinoid is selected from the group consisting of retinoic acid, retinol, retinol esters, hyaluronic acid and/or collagen.

Inhibition of Tooth Wear

The involuntary grinding of teeth characteristic of true bruxism is caused by involuntary contractions of the masseter, temporalis and pterygoid muscles. The masseter and temporalis usually are targeted as the muscles which will undergo chemodenervation. They are injected so as to limit the penetration of the subject postsynaptically targeted chemodenervation polypeptides to the volume and body of the muscles. Diffusion should preferably be limited to a distance of no more than 25 to 35 mms. Preferably, a unit dose injection is given at the surface of each of these muscles at multiple points percutaneously or permucosally. Of course, appropriate dental evaluation to assess the degree of damage or potential damage to the teeth should be conducted prior to application of the subject polypeptides.

Stroke and Cerebro-Spinal Injury

Cerebrovascular injuries (stroke and cerebro-spinal injury) can cause spasticity and contractions as a result of paralysis and spasticity. Although the subject postsynaptically targeted chemodenervation polypeptides produce a paralysis, they can be useful in reducing muscle mass and in helping spasticity. Symptomatic spasticity can result in chronic involuntary movements as well as difficulties with contracted postures or contractions of the limbs. The application of the subject polypeptides to these spastic states involves knowledge of innervation zones of limb muscles. The muscle which is involved in the abnormal posture or abnormal movement can be identified with an electromyographic needle. Such muscles can also be identified as causing the posture deformities based on experience and an understanding of the muscle's contractile states on the limb position and movement capabilities. These muscles are impaled with a needle at a site close to the innervation zone. In certain situations, it may be necessary to stimulate the muscle with a stimulating current through a teflon coated electromyographic needle to insure the correct placement of the injections. The subject postsynaptically targeted chemodenervation polypeptide is injected at a dose level appropriate to create a field of denervation encompassing the innervation zone of the muscle or the entire muscle. Multiple injections over long muscles may be necessary to isolate the effect over that muscle.

Cerebral Palsy

Cerebral palsy results from various forms of brain damage related to anoxia or vascular insufficiency, usually at the time of birth. The destruction of the central cortex of the central motor system results in involuntary movement spasticity, abnormal posturing, and unwanted contractures of muscles. Physical therapy and occasionally antispasmodic drugs are used to treat cerebral palsy. In situations where spasticity is involved with pain, deformity, involuntary movements, or limitations in functional capabilities of a patient, use of the subject postsynaptically targeted chemodenervation polypeptides may be indicated. Application involves targeting muscle groups vital to the patient's disability such as muscles which produce limb deformities or impairments in the volitional movements, or in situations where contractures seem to be developing into abnormal postures.

The dosage for treatment of this disease will involve targeting these muscles and using a formulation similar to that used to treat cerebrovascular disease. The prototype for large muscle applications is spasmotic torticollis. The targeted muscle is injected with a dose sufficient to encompass the innervation zone of the muscle.

Multiple Sclerosis

Multiple sclerosis is a disease of white matter of the central nervous system. It involves a demyelination process which leads to impairment of the cortical spinal track and associative tracks in the brain stem. This leads to spinal damage and resultant spasticity. Spasticity in multiple sclerosis can be debilitating because of involuntary movement, contracture, posture deformities, and in certain situations, pain. Such muscle spasticity may be treated with the subject postsynaptically targeted chemodenervation polypeptides.

Again, the subject postsynaptically targeted chemodenervation polypeptide is targeted at muscles determined by the physician, neurologist, podiatrist or orthopedic surgeon that appear to be hyperactive. The muscles are injected with a quantity sufficient to encompass volumetrically the muscle or its innervation zone, or both. A working knowledge of muscle anatomy, innervation, and functional anatomy will be needed by the practitioner to achieve optimum results.

Parkinson's Disease

Parkinson's disease is characterized by three basic defects: akinesia (lack of movement); tremor (involuntary movement); and rigidity (increase muscle tone in muscle groups). The subject postsynaptically targeted chemodenervation polypeptides can be used to improve the degree of tremor and rigidity present in Parkinson's disease although use of the subject polypeptides may be contraindicated in akinesia.

In certain situations in Parkinson's disease, severe dystonias develop in the patient's limbs. In these situations, the involuntary movements are exaggerated, spastic, and often painful. The subject postsynaptically targeted chemodenervation polypeptide is injected into the muscle in a dose sufficient to encompass the volume of the muscle or its innervation zone or both. It is preferably done with a stimulating electrode needle to an EMG machine or in conjunction with EMG machine to insure the correct placement of the needle in the muscle. The subject postsynaptically targeted chemodenervation polypeptide is preferably given in multiple injection points for large muscles in order to insure an adequate percentage of the innervation zone is encompassed.

Headaches

Tension headaches can originate in skeletal muscular stress, as disclosed in U.S. Pat. No. 5,714,468. The subject postsynaptically targeted chemodenervation polypeptides can be employed to help alleviate the headache symptoms by targeting the implicated muscles for chemodenervation.

Surgery

Temporary Paralysis

As used herein, "temporary paralysis", or "transient paralysis" refers to many different possible periods of time during which a targeted muscle exhibits paralysis in response to contact with a postsynaptically targeted chemodenervation polypeptide of the invention. The invention provides a number of such postsynaptically targeted chemodenervation polypeptides with a range of potencies. Without being bound by theory, the duration of paralysis depends on the binding kinetics of the particular polypeptide, the number of available muscle nAChRs, the dynamics of receptor turnover and new receptor presentation, and the threshold signal for muscle activity. Accordingly, a shorter duration of paralysis can be achieved by, for example, using a relatively low potency postsynaptically targeted chemodenervation polypeptide, administering a small amount of the polypeptide so as to reduce receptor occupancy over an area of muscle to that minimally required for effect, administering the polypeptide for a short period of time so as to reduce receptor occupancy over an area of muscle over time to that minimally required for effect, or performing a single administration or infrequent administrations of the polypeptide, or a combination of these approaches. For example, a short chain α-neurotoxin may be selected for use, rather than a modified long chain α-neurotoxin exhibiting a higher affinity for α-1 nAChR and/or exhibiting irreversible binding to α-1 nAChR. Within the group of potential short chain α-neurotoxins a species with relatively low affinity for the α-1 nAChR may also be selected. Conversely, to achieve a longer duration of paralysis, a relatively potent modified long chain α-neurotoxin may be used, a larger amount of toxin may be used to increase receptor occupancy over an area of muscle, the period of administration (e.g., sustained administration) may be increased to increase receptor occupancy over an area of muscle over time, or repeated administrations may be done, or a combination of these approaches may be used.

Formulation and Administration

A variety of administration routes are available. The particular mode selected will depend, of course, upon the nature of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Typically such modes of administration include parenteral routes. The term "parenteral" includes subcutaneous, intramuscular, intradermal, transdermal or topical infusion. Transdermal, subcutaneous and intramuscular routes are most preferred. Oral and intravenous administration should be avoided due to the toxicity associated with the agents of the invention.

Accordingly, the postsynaptically targeted chemodenervation polypeptide may be administered by means of intramuscular injection directly into a local area such as a spastic muscle, preferably in the region of the neuromuscular junction. Alternatively, subcutaneous delivery may be employed to deliver the postsynaptically targeted chemodenervation polypeptide directly to the affected region, where appropriate. Advantageously, transdermal delivery and/or conventional microinjection techniques may be employed for impacting skeletal muscles in close proximity to the skin, as described herein. The postsynaptically targeted chemodenervation polypeptide can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added, stabilizers such as human serum albumin may also be included. The formulation may be preserved by means of a suitable pharmaceutically acceptable preservative such as a paraben, although preferably it is unpreserved.

It is preferred that the postsynaptically targeted chemodenervation polypeptide is formulated in unit dosage form; for example, it can be provided as a sterile solution in a vial or as a vial or sachet containing a lyophilized powder for reconstituting a suitable vehicle such as saline for injection.

The dose of postsynaptically targeted chemodenervation polypeptide administered to the patient will depend upon the severity of the condition; e.g., the number of muscle groups requiring treatment, the age and size of the patient and the potency of the toxin. The potency of the toxin is expressed as a multiple of the $LD_{50}$ value for the mouse, one unit (U) of polypeptide being defined as being the equivalent to that amount, on a per mouse basis, that kills 50% of a group of Swiss-Webster mice weighing between 17 and 22 grams.

The dosages used in human therapeutic applications are roughly proportional to the mass of muscle being injected. Typically, the dose administered to the patient may be up from about 0.01 to about 1,000 units; for example, up to about 500 units, and preferably in the range from about 80 to about 460 units per patient per treatment, although smaller or larger doses may be administered in appropriate circumstances.

As the physicians become more familiar with the use of this product, the dose may be changed. Both the quantity of the subject postsynaptically targeted chemodenervation polypeptide administered and the frequency of its administration will be at the discretion of the physician responsible for the treatment and will be commensurate with questions of safety and the effects produced by the particular polypeptide and the mode of administration.

Advantageously, the subject postsynaptically targeted chemodenervation polypeptides lack a latency period between administration and paralysis. Accordingly, an effective dosage is immediately determinable. The administrator may initiate treatment with a first dosage and upon finding paralysis to be below the desired level may increase the dosage stepwise in order to achieve the desired level or extent of paralysis.

Pharmaceutical Compositions

A postsynaptic chemodenervation polypeptide of the invention may be administered alone or as part of a pharmaceutical composition. Such a pharmaceutical composition may include the subject postsynaptically targeted chemodenervation polypeptide in combination with any standard physiologically and/or pharmaceutically acceptable carriers which are known in the art. See, for example, Remington's Pharmaceutical Sciences, 18th Ed. (1990, Mack Publishing Co., Easton, Pa.). The carrier may take a wide variety of forms depending on the form of preparation desired for administration, e.g., intramuscular, subcutaneous or parenteral. The compositions may further contain antioxidizing agents, stabilizing agents, preservatives and the like. The compositions should be sterile and contain a therapeutically effective amount of the subject postsynaptically targeted chemodenervation polypeptide in a unit of weight or volume suitable for administration to a patient.

The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material, that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials well known in the art.

Compositions suitable for parenteral administration conveniently comprise sterile aqueous and non-aqueous preparations of the subject postsynaptically targeted chemodenervation polypeptides. This aqueous preparation may be formulated according to known methods using suitable dispersing or wetting agents and suspending agents. Aqueous carriers include water, alcoholic/aqueous solutions, emulsions or suspensions, including saline and buffered media. Examples of non-aqueous solvents are propylene glycol, polyethylene glycol, vegetable oils such as olive oil, and injectable organic esters such as ethyl oleate, and including synthetic mono- or di-glycerides. The sterile injectable preparation also may be a sterile injectable solution or suspension in a non-toxic parenterally-acceptable diluent or solvent, for example, as a solution in 1,3-butane diol. In addition, fatty acids such as oleic acid may be used in the preparation of injectables. Preferred parenteral vehicles include sodium chloride solution, Ringers dextrose, dextrose and sodium chloride, lactated Ringers or fixed oils. Carrier formulations suitable for subcutaneous, intravenous, intramuscular, etc. administrations can be found in Remington's Pharmaceutical Sciences, Mack Publishing Co., Easton, Pa. Preservatives and other additives may also be present such as, for example, antimicrobials, anti-oxidants, chelating agents, and inert gases and the like.

The pharmaceutical compositions may conveniently be presented in unit dosage form in packages, kits and the like together with instructions for use and may be prepared by any of the methods well-known in the art of pharmacy. All methods include the step of bringing the subject postsynaptically targeted chemodenervation polypeptides of the invention into association with a carrier which constitutes one or more accessory ingredients. In general, the compositions are prepared by uniformly and intimately bringing the subject postsynaptically targeted chemodenervation polypeptides into association with a liquid carrier, a finely divided solid carrier, or both, and then, if necessary, shaping the product.

Other delivery systems can include time-release, delayed release or sustained release delivery systems. Such systems can avoid repeated administrations of the subject postsynaptically targeted chemodenervation polypeptides, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the α-neurotoxin molecule is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Also provided by the invention are chemically modified derivatives of the subject postsynaptically targeted chemodenervation polypeptides which may provide additional advantages such as increased solubility, stability and circulating time of the polypeptide, or decreased immunogenicity (see, e.g., U.S. Pat. No. 4,179,337). Accordingly, the invention encompasses derivatization of the subject postsynaptically targeted chemodenervation polypeptides, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics™, commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized long-chain α-neurotoxins of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

The chemical moieties for derivatization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

In some embodiments, chemical derivatization of the subject postsynaptically targeted chemodenervation polypeptides of the present invention is performed using a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term “about” indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize the subject postsynaptically targeted chemodenervation polypeptides, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the subject postsynaptically targeted chemodenervation polypeptides via alkylation or acylation reactions.

The polyethylene glycol molecules (or other chemical moieties) should be attached to the subject postsynaptically targeted chemodenervation polypeptides with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the subject postsynaptically targeted chemodenervation polypeptides can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivatization include saccharides that can be attached to the subject postsynaptically targeted chemodenervation polypeptides via alkylation or acylation reactions. Derivatization with polysaccharides, e.g., chitosan, is also included.

Moreover, the invention also encompasses derivatization of the subject postsynaptically targeted chemodenervation polypeptides, for example, with lipids (including cationic, anionic, polymerized, charged, synthetic, saturated, unsaturated, and any combination of the above, etc.). stabilizing agents.

Moreover, the invention encompasses additional modifications of the subject postsynaptically targeted chemodenervation polypeptides. Such additional modifications are known in the art, and are specifically provided, in addition to methods of derivatization, etc., in U.S. Pat. No. 6,028,066, which is hereby incorporated in its entirety herein.

Significantly, and unlike the botulinum toxins conventionally employed in the art, the subject postsynaptic chemodenervation polypeptides may also be advantageously administered by way of transdermal delivery in view of the significant size reduction and stability improvements obtained with the present polypeptides. Biocompatible implants such as those described in U.S. Pat. Nos. 6,306,423 and 6,312,708 may find advantageous use, as well as transdermal patch systems (such as, e.g., U.S. Patent Publication 2004/0009180) and solid solution perforators (such as e.g., U.S. Patent Publication 2006/0074376), and the like. Conventional microinjection techniques such as those described by Martanto et al., Pharm. Res. 21:947 (2004); Wang et al., J. Inv. Derm. 126:1080-87 (2006) and Xie et al., Nanomedicine, Biotechnology and Medicine, 1:1-190 (200) may also be used in conjunction with the α-neurotoxin compositions and methods provided herein. Ultrasound techniques such as those described by Mitragotri et al., Science 5225:850-853 (1995) may also be employed with the compositions and methods described herein.

Additionally, or alternatively, co-administration of peptide chaperones such as described by Chen et al. Nature Biotechnology, 24:455-60 (2006) and/or Prausnitz, Nature Biotechnology 24:416-17 (2006) may also find advantageous use. In one embodiment, co-administration with the transdermal peptide sequence ACSSSPSKHCG (SEQ ID NO:94) is specifically contemplated, as it has already been shown to facilitate efficient transdermal protein drug delivery through intact skin of a similarly-sized protein molecule. See Chen et al., supra.

The subject postsynaptically targeted chemodenervation polypeptides may be administered alone or in combination (co-administered) with the above-described drug therapies by any conventional route, including injection, repeated injection, topical application, etc., over time. The administration may, for example, be intraperitoneal, intramuscular, intra-cavity, subcutaneous, or transdermal. When using the subject postsynaptically targeted chemodenervation polypeptides, direct administration to the affected site (e.g., muscles with involuntary spasm, wrinkle, etc.) such as administration by injection, is preferred.

The term "co-administered," means administered substantially simultaneously with another agent. By substantially simultaneously, it is meant that a postsynaptically targeted chemodenervation polypeptide is administered to the subject close enough in time with the administration of the other agent (e.g., an anti-wrinkling agent, etc.). The other agent may be present in a different formulation than the postsynaptically targeted chemodenervation polypeptide, or it may be part of the same formulation.

The co-administered agent can act cooperatively, additively or synergistically with the subject postsynaptically targeted chemodenervation polypeptide to produce a desired effect, for example, lessening of wrinkles. The other agent is administered in effective amounts. Such amounts maybe less than these sufficient to provide a therapeutic benefit when the agent is administered alone and not in combination with the subject postsynaptically targeted chemodenervation polypeptides. A person of ordinary skill in the art would be able to determine the effective amounts needed.

The invention will be more fully understood by reference to the following examples. These examples, however, are merely intended to illustrate the embodiments of the invention and are not to be construed to limit the scope of the invention.

TABLE 1

Disclosed below are long-chain α-neurotoxin polypeptides. Isolated and/or modified forms of these polypeptides can be employed in conjunction with the compositions and methods described herein.

| Species | Seq Id# | Sequence |
|---|---|---|
| *Naja kaouthia* | 1 | IRCFITPDITSKDCPNGHVCYTKTWCDAFCSIRGKRVDLGCAATCPTV KTGVDIQCCSTDNCNPFPTRKRP |
| *Naja kaouthia* | 2 | IRCFITPDITSKDCPNGHVCYTKTWCDAFCSIRGKGVDLGCAATCPTV KTGVDIQCCSTDNCNPFPTRKRP |
| *Naja kaouthia* | 3 | IRCFITPDITSKDCPNGHVCYTKTWCDAFCSIRGKRVDLGCAATCPTV KTGVDIQCCSTDNCT |
| *Naja kaouthia* | 4 | IRCFITPDITSKDCPNGRVCYTKTWCDAFRSIRGKRVDLGCAATCPTV KTGVDIQCCSTDNCNPFPTRKRP |
| *Naja naja* | 5 | IRCFITPDITSKDCPNGHVCYTKTWCDAFCSIRGKRVDLGCAATCPTV KTGVDIQCCSTDDCDPFPTRKRP |
| *Naja naja* | 6 | IRCFITPDITSKDCPNGHVCYTKTWCDGFCSIRGKRVDLGCAATCPTV RTGVDIQCCSTDDCDPFPTRKRP |
| *Naja naja* | 7 | IRCFITPDITSKDCPNGHVCYTKTWCDGFCRIRGERVDLGCAATCPTV KTGVDIQCCSTDDCDPFPTRKRP |
| *Naja naja* | 8 | IRCFITPDITSKDCPNGHVCYTKTWCDGFCSRRGERVDLGCAATCPT VKTGVDIQCCSTDDCDPFPTRKRP |
| *Naja naja* | 9 | IRCFITPDITSKDCPNGHVCYTKTWCDGFCSSRGKRVDLGCAATCPT VRTGVDIQCCSTDDCDPFPTRKRP |
| *Naja sputatrix* | 10 | IRCFITPDVTSTDCPNGHVCYTKTWCDGFCSSRGRRVELGCAATCPT VKPGVDIQCCSTDNCNPFPTRP |
| *Naja haje haje* | 11 | IRCFITPDVTSQACPDGQNICYTKTWCDNFCGMRGKRVDLGCAATCP TVKPGVDIKCCSTDNCNPFPTRERS |
| *Naja haje haje* | 12 | IRCFITPDVTSQACPDGHVCYTKMWCDNFCGMRGKRVDLGCAATCP TVKPGVDIKCCSTDNCNPFPTRKRS |
| *Naja oxiana* | 13 | ITCYKTPIPITSETCAPGQNLCYTKTWCDAWCGSRGKVIELGCAATCP TVESYQDIKCCSTDDCNPHPKQKRP |
| *Naja nivea* | 14 | IRCFITPDVTSQACPDGHVCYTKMWCDNFCGMRGKRVDLGCAATCP KVKPGVNIKCCSRDNCNPFPTRKRS |

TABLE 1-continued

Disclosed below are long-chain α-neurotoxin polypeptides. Isolated and/or modified forms of these polypeptides can be employed in conjunction with the compositions and methods described herein.

| Species | Seq Id# | Sequence |
|---|---|---|
| *Naja melanoleuca* | 15 | IRCFITPDVTSQICADGHVCYTKTWCDNFCASRGKRVDLGCAATCPT VKPGVNIKCCSTDNCNPFPTRNRP |
| *Naja melanoleuca* | 16 | KRCYRTPDLKSQTCPPGEDLCYTKKWCADWCTSRGKVIELGCVATC PKVKPYEQITCCSTDNCNPHPKMKP |
| *Ophiophagus hannah* | 17 | TKCYVTPDVKSETCPAGQDICYTETWCDAWCTSRGKRVDLGCAATC PIVKPGVEIKCCSTDNCNPFPTWRKRP |
| *Ophiophagus hannah* | 18 | TKCYVTPDATSQTCPDGQDICYTKTWCDGFCSSRGKRIDLGCAATCP KVKPGVDIKCCSTDNCNPFPTWKRKH |
| *Ophiophagus Hannah* | 19 | TKCYVTPDVKSETCPAGQDLCYTETWCVAWCTVRGKRVSLTCAAICP IVPPKVSIKCCSTDACGPFPTWPNVR |
| *Ophiophagus Hannah* | 20 | TKCYKTGDRIISEACPPGQDLCYMKTWCDVFCGTRGRVIELGCTATC PTVKPHEQITCCSTDNCNPHPKMKQ |
| *Ophiophagus Hannah* | 21 | TKCYKTGDRIISEACPPGQDLCYMKTWCDVFCGTRGRVIELGCTATC PTVKPHEQITCCSTDNCDPHHKMLQ |
| *Ophiophagus Hannah* | 22 | LICFISSHDSVTCAPGENVCFLKSWCDAWCGSRGKKLSFGCAATCPK VNPGIDIECCSTDNCNPHPKLRP |
| *Ophiophagus Hannah* | 23 | TKCYVTPDVKSETCPAGQDICYTETWCDAWCTSRGKRVNLGCAATC PIVKPGVEIKCCSTDNCNPFPTRKRP |
| *Ophiophagus Hannah* | 24 | TKCYVTPDATSQTCPDGENICYTKSWCDVFCSSRGKRIDLGCAATCP KVKPGVDIKCCSTDNCNPFTPWKRH |
| *Ophiophagus Hannah* | 25 | TKCYITPDVKSETCPDGENICYTKTWCDVWCGSRGRRVDLGCAATC PIVKPGVNINCCSTDNCNPFPKRS |
| *Ophiophagus Hannah* | 26 | TKCYVTPDVTSQTCPDGQNICYTETWCDAWCGSRGKRVNLGCAATC PKVNPGVDIICCSTDNCNPFPKRS |
| *Ophiophagus Hannah* | 27 | TKCYVTPDVKSETCPDGENICYTKSWCEVFCTSRGKRIDLGRAATCP KVKPGVDIKCCSTDNCNPFTPWKRH |
| *Ophiophagus Hannah* | 28 | TKCYITPDVKSETCPDGENICYTKSWCDVFCTSRGKRIDLGCAATCPK VKPGVDIKCCSTDNCNPFTPWKRH |
| *Ophiophagus Hannah* | 29 | LICFISPHDSVTCAPGENVCFLKSWCDAWCGSRGKKLSFGCAATCPK VNPGIDIECCSTDNCNPHPKLRP |
| *Ophiophagus Hannah* | 30 | LICFISSHDSVTCAPGENVCFLKSWCDAWCGSRGKKLSFGCAATCPK VNPGIDIECCSTDNCNPHPKLRP |
| *Ophiophagus Hannah* | 31 | RICHKSSFISETCPDGQNLCYLKSWCDIFCGSRGERLEFGCAATCPEV KPGVNIECCSTDNCNPHPKLRP |
| *Ophiophagus Hannah* | 32 | TKCYKTGERIISETCPPGQDLCYMKTWCDVFCGSRGRVIELGCTATC PTVKPHEQITCCSTDNCNPHPKMKQR |
| *Ophiophagus Hannah* | 33 | TKCYKTGERIISETCPPGQDLCYMKTWCDVFCGSRGRVIELGCTATC PTVKHHEQITCCSTDNCNPHPKMKQR |
| *Ophiophagus Hannah* | 34 | TKCYKTGERIISETCPPGQDLCYMKTWCDVFCGSRGRVVELGCTATC PTVKPHEQITCCSTDNCNPHPKMKQR |
| *Ophiophagus Hannah* | 35 | LTNAPDSWSSRRTCLCPAWVPLRSRPVAGHSKQCGSRGRRVDLGC AATCPIVKPGVNINCCSTDNCNPFPKRS |
| *Pseudonaja textilis* | 36 | RTCFITPDVKSKPCPPGQEVCYTETWCDGFCGIRGKRVELGCAATCP TPKKTGIDIQCCSTDDCNTFPLRP |
| *Pseudonaja textilis* | 37 | RTCFITPDVKSKPCPPGQEVCYTKTWCDGFCGIRGKRVDLGCAATCP TPKKTGIDIICCSTDDCNTFPLRPRGRLSSIKDHP |
| *Dendroaspis viridis* | 38 | RTCYKTPSVKPETCPHGENICYTETWCDAWCSQRGKRVELGCAATC PKVKAGVGIKCCSTDNCNPFPVWNPRG |

TABLE 1-continued

Disclosed below are long-chain α-neurotoxin polypeptides. Isolated and/or modified forms of these polypeptides can be employed in conjunction with the compositions and methods described herein.

| Species | Seq Id# | Sequence |
|---|---|---|
| *Dendroaspis jamesoni* | 39 | RTCYKTYSDKSKTCPRGEDICYTKTWCDGFCSQRGKRVELGCAATC PKVKTGVEIKCCSTDYCNPFPVWNPR |
| *Dendroaspis viridis* | 40 | RTCYKTPSVKPETCPHGENICYTETWCDAWCSQRGKREELGCAATC PKVKAGVGIKCCSTDNCDPFPVKNPR |
| *Dendroaspis viridis* | 41 | RTCYKTPSVKPETCPHGENICYTETWCDAWCSQRGKRVELGCAATC PKVKAGVGIKCCSTDNCNPFPVWNPR |
| *Dendroaspis polylepis* | 42 | RTCNKTFSDQSKICPPGENICYTKTWCDAWCSQRGKRVELGCAATC PKVKAGVEIKCCSTDDCDKFQFGKPR |
| *Dendroaspis polylepis* | 43 | RTCNKTPSDQSKICPPGENICYTKTWCDAWCSQRGKIVELGCAATCP KVKAGVEIKCCSTDNCNKFKFGKPR |
| *Dendroaspis polylepis* | 44 | RTCNKTFSDQSKICPPGENICYTKTWCDAWCSRRGKIVELGCAATCP KVKAGVGIKCCSTDNCNLFKFGKPR |
| *Acanthophis antarcticus* | 45 | VICYRGYNNPQTCPPGENVCFTRTWCDAFCSSRGKVVELGCAATCPI VKSYNEVKCCSTDKCNPFPVRPRRPP |
| *Acanthophis antarcticus* | 46 | VICYRKYTNNVKTCPDGENVCYTKMWCDGFCTSRGKVVELGCAATC PIRKPGNEVKCCSTNKCNHPPKRKKRRP |
| *Aspidelaps scutatus* | 47 | RICYIAPYDHKTCAAGENICYLKAWCDAWCSSRGKKLEFGCAATCPT VKPGVDISCCDTDNCNPHPKL |
| *Astrotia stokesii* | 48 | LSCYLGYKHSQTCPPGENVCFVKTWCDGFCNTRGERIIMGCAATCPT AKSGVHIACCSTDNCNIYAKWGS |
| *Astrotia stokesii* | 49 | LSCYLGYKHSQTCPPGENVCFVKTWCDAFCSTRGERIVMGCAATCP TAKSGVHIACCSTDNCNIYTKWGSGR |
| *Austrelaps superbus* | 50 | LICYVDSKTSRTCPPGENVCFTETWCDARCSLLGKRVDLGCAATCPT AKPGVDITCCSTDKCNPFPTQKHR |
| *Austrelaps superbus* | 51 | FSCYKTPDVKSEPCAPGENLCYTKTWCDRFCSIRGKVIELGCAATCP PAEPRKDITCCSTDNCNPHPAH |
| *Bungarus candidus* | 52 | LLCYKTPSPINAETCPPGENLCYTKMWCDAWCSSRGKVVELGCAAT CPSKKPYEEVTCCSTDKCNPHPKQRPD |
| *Bungarus candidus* | 53 | LLCYKTPSPINAETCPPGENLCYTKMWCDAWCSSRGKVIELGCAATC PSKKPYEEVTCCSTDKCNPHPKQRPG |
| *Bungarus candidus* | 54 | LLCYKTPIPINAETCPPGENLCYTKMWCDIWCSSRGKVVELGCAATCP SKKPYEEVTCCSTDKCNPHPKQRPD |
| *Bungarus candidus* | 55 | IVCHTTATSPISAVTCPPGENLCYRKMFCDAICSSRGKVVELGCAATC PSKKPYEEVTCCSNDKCNPHPKQRPG |
| *Boulengerina annulata* | 56 | IRCFITPRVSSQACPDGHVCYTKTWCDNFCGINGKRVDLGCAATCPT VKPGVDIKCCSTDNCNPFPTRKRP |
| *Bungarus flaviceps* | 57 | RTCLISPSSTSQTCPKGQDICFTKAFCDRWCSSRGPVIEQGCAATCP EFTSRYKSLLCCTTDNCNH |
| *Bungarus multicinctus* | 58 | IVCHTTATSPISAVTCPPGENLCYRKMWCDAFCSSKGKVVELGCAAT CPSKKPYEEVTCCSTDKCNPHPKQRPG |
| *Bungarus multicinctus* | 59 | IVCHTTATSPISAVTCPPGENLCYRKMWCDAFCSSRGKVVELGCAAT CPSKKPYEEVTCCSTDKCNPHPKQRPG |
| *Bungarus multicinctus* | 60 | IVCHTTATSPISAVTCPPGENLCYRKMWCDAFCSSRGKVVELGCAAT CPSKKPYEEVTCCSTDQCHPHPKQRPG |
| *Bungarus multicinctus* | 61 | IVCHTTATSPISAVTCPPGENLCYRKMWCDVFCSSRGKVVELGCAAT CPSKKPYEEVTCCSTDKCNPHPKQRPG |
| Demansia *vestigiata* | 62 | RTCLKTPEVKSEPCPPGQEVCYTKAWCDRMCSFRGKVIELGCAATC PRQEPGKEITCCSTDDCNTHP |

TABLE 1-continued

Disclosed below are long-chain α-neurotoxin polypeptides. Isolated and/or modified forms of these polypeptides can be employed in conjunction with the compositions and methods described herein.

| Species | Seq Id# | Sequence |
|---|---|---|
| *Demansia vestigiata* | 63 | RTCLKTPEVKSEPCPPGQEVCYTKAWRDRMCSFRGKVIELGCAATC PRQEPGKEITCCSTDDCNTHP |
| *Laticauda laticaudata* | 64 | RICFKTPYVKSETCPPGQELCYTKTWCDRFCSIRGKVIELGCTATCPR AEPKEDTTCCSKDNCNPHP |
| *Laticauda colubrina* | 65 | RICYLAPRDTQICAPGQEICYLKSWDDGTGSIRGNRLEFGCAATCPTV KRGIHIKCCSTDKCNPHPKLA |
| *Laticauda colubrina* | 66 | RICYLAPRDTQICAPGQEICYLKSWDDGTGFLKGNRLEFGCAATCPTV KPGIDIKCCSTDKCNPHPKLA |
| *Lapemis hardwickii* | 67 | LSCYLGYKRSQTCPPGEKVCFVKSWCDAFCGSRGKRIEMGCAATCP TVKDGIDITCCATDNCNTYANWGSG |
| *Lapemis hardwickii* | 68 | RTCYRTHPYKPETCPPGQNLCYKKSWCDAFCSSRGKVIELGCTAKC PTVKHGKDINCCATDNCNTVANWKSR |
| *Laticauda semifasciata* | 69 | RECYLNPHDTQTCPSGQEICYVKSWCNAWCSSRGKVLEFGCAATCP SVNTGTEIKCCSADKCNTYP |
| *Laticauda semifasciata* | 70 | RECYLNPHDTQTCPSGQEICYVKSWCNAWCSSRGKVLEFGCAATCP SVNTGTEIKCCSADKCNTYP |
| *Notechis scutatus* | 71 | LICYMGPKTPRTCPRGQNLCYTKTWCDAFCSSRGKVVELGCAATCPI AKSYEDVTCCSTDNCNPFPVRPRHPP |
| *Oxyuranus scutellatus* | 72 | RRCFTTPSVRSERCPPGQEVCYTKTWTDGHGGSRGKRVDLGCAAT CPTPKKKDIKIICCSTDNCNTFPKWP |
| *Oxyuranus microlepidotus* | 73 | RRCFITPDVRSERCPPGQEVCYTKTWCDGFCSSRGKRVDLGCAATC PTPKKKGIDIICCSKDNCNTFPKWP |
| *Oxyuranus microlepidotus* | 74 | RRCFITPDVRSERCPPGQEVCYTKTWCDGFCGSRGKRVDLGCAATC PTPKKKGIDIICCSKDNCNTFPKWP |
| *Oxyuranus microlepidotus* | 75 | RRCFTTPSVRSERCPPGQEVCYTKTWTDGHGGSRGKRVDLGCAAT CPTPKKKDIKTICCSKDNCNTFPKWP |
| *Oxyuranus microlepidotus* | 76 | RRCFITPDVRSERCPPGQEVCYTKTWCDGFCGSRGKRVDLGCAATC PTPKKKDIKIICCSKDNCNTFPKWP |
| *Pseudechis australis* | 77 | LTCYKGRDRSSETCRSEQELCCTKTWCDQWCQDRGPRLEMGCTAT CPRRMPGLDFTCCTTDNCNPVPT |
| *Pseudechis australis* | 78 | LTCYKGRDRSSETCRSEQELCCTKTWCDQWCQDRGPRLEMGCTAT CPRRMPGLDFTCCTTDNCNPVPT |
| *Tropidechis carinatus* | 79 | FSCYKTPHVKSEPCAPGQNLCYTKTWCDAFCFSRGRVIELGCAATCP PAEPKKDISCCSTDNCNPHPAHQSR |

TABLE 2

Disclosed are native long-chain α-neurotoxin polypeptides, lacking the fifth disulfide bond in the tip region of loop II, which can be employed in conjunction with the compositions and methods described herein.

| Species | Seq Id# | Sequence |
|---|---|---|
| *Naja kaouthia* | 4 | IRCFITPDITSKDCPNGRVCYTKTWCDAFRSIRGKRVDLGCAATCPTV KTGVDIQCCSTDNCNPFPTRKRP |
| *Ophiophagus Hannah* | 35 | LTNAPDSWSSRRTCLCPAWVPLRSRPVAGHSKQCGSRGRRVDLGC AATCPIVKPGVNINCCSTDNCNPFPKRS |

TABLE 2-continued

Disclosed are native long-chain α-neurotoxin polypeptides, lacking the fifth disulfide bond in the tip region of loop II, which can be employed in conjunction with the compositions and methods described herein.

| Species | Seq Id# | Sequence |
|---|---|---|
| *Demansia vestigiata* | 63 | RTCLKTPEVKSEPCPPGQEVCYTKAWRDRMCSFRGKVIELGCAATC PRQEPGKEITCCSTDDCNTHP |
| *Laticauda colubrina* | 65 | RICYLAPRDTQICAPGQEICYLKSWDDGTGSIRGNRLEFGCAATCPTV KRGIHIKCCSTDKCNPHPKLA |
| *Laticauda colubrine* | 66 | RICYLAPRDTQICAPGQEICYLKSWDDGTGFLKGNRLEFGCAATCPTV KPGIDIKCCSTDKCNPHPKLA |
| *Oxyuranus scutellatus* | 72 | RRCFTTPSVRSERCPPGQEVCYTKTWTDGHGGSRGKRVDLGCAAT CPTPKKKDIKIICCSTDNCNTFPKWP |
| *Oxyuranus microlepidotus* | 75 | RRCFTTPSVRSERCPPGQEVCYTKTWTDGHGGSRGKRVDLGCAAT CPTPKKKDIKTICCSKDNCNTFPKWP |

TABLE 3

Disclosed are short-chain α-neurotoxin polypeptides. Isolated and/or modified forms of these polypeptides can be employed in conjunction with the compositions and methods described herein.

| Species | Seq Id# | Sequence |
|---|---|---|
| *Naja kaouthia* | 80 | LECHNQQSSQTPTTTGCSGGETNCYKKRWRDHRGYRTERGCGCPS VRNGIEINCCTTDRCNN |
| *Naja kaouthia* | 81 | LECHNQQSSQAPTTKTCSGGETNCYKKRWRDHRGYRTERGCGCPS VRNGIEINCCTTDRCNN |
| *Naja kaouthia* | 82 | LECHNQQSSQAPTTKTCSGETNCYKKWWSDHRGTIIERGCGCPKVK PGVNLNCCRTDRCNN |
| *Naja kaouthia* | 83 | LECHNQQSSQTPTTKTCSGETNCYKKWWSDHRGTIIERGCGCPKVK PGVNLNCCRRDRCNN |
| *Naja oxiana* | 84 | LECHNQQSSQPPTTKTCSGETNCYKKWWSDHRGTIIERGCGCPKVK PGVNLNCCRTDRCNN |
| *Micrurus nigrocinctus* | 85 | MICHNQQSSQPPTIKTCSEGQCYKKTWRDHRGTISERGCGCPTVKP GIHISCCASDKCNA |
| *Pseudonaja textilis* | 86 | LTCYKSLSGTVVCKPHETICYRRLIPATHGNAIIDRGCSTSCPGGNRPV CCSTDLCNK |
| *Pseudonaja textilis* | 87 | LTCYKRYFDTVVCKPQETICYRYIIPATHGNAITTRGCSTSCPSGIRLV CCSTDLCNK |
| *Pseudonaja textilis* | 88 | LTCYKGYHDTVVCKPHETICYRYLVPATHGNAIPARGCGTSCPGGNH PVCCSTDLCNK |
| *Naja pallida* | 89 | LECHNQQSSQPPTTKTCPGETNCYKKVWRDHRGTIIERGCGCPTVK PGIKLNCCTTDKCNN |
| *Naja haje anulifera* | 90 | LECHNQQSSQPPTTKTCPGETNCYKKRWRDHRGSITERGCGCPSVK KGIEINCCTTDKCNN |
| *Acalyptophis peroni* | 91 | MTCCNQQSSQPKTTTNCAGNSCYKKTWSDHRGTIIERGCGCPQVKS GIKLECCHTNECNN |
| *Dendroaspis polylepis* | 92 | RICYNHQSTTRATTKSCEENSCYKKYWRDHRGTIIERGCGCPKVKPG VGIHCCQSDKCNY |
| *Pseudechis australis* | 93 | MTCCNQQSSQPKTTTICAGGESSCYKKTWSDHRGSRTERGCGCPH VKPGIKLTCCKTDECNN |

EXPERIMENTAL

Example 1: Molecular Cloning of cDNAs Encoding α-Neurotoxins from Snake Venom Glands The following experimental procedure exemplifies the molecular cloning of the long chain alpha neurotoxin-coding cDNA pool using the Asian Cobra *Naja kaouthia* as the biological source. One skilled in the art understands that this procedure with the universal neurotoxin primer sequences provided can be used for cloning analogous sequences from any species of the Elapidae and Hydrofilidae taxons.

The venom glands of a single *N. kaouthia* specimen were surgically removed from the skull immediately after decapitation of the animal. The extracted glands were quickly dissected with a razor blade on a Petri dish placed on ice. The dissected gland tissue was transferred into a 2 ml Eppendorf tubes containing lysis buffer (10 ul buffer per 1 mg tissue). The lysis of the gland tissue was completed by vortexing the lysis suspension on a Thermomixer (Eppendorf AG, Hamburg Germany) at maximum speed at 4° C. for 30 minutes. Total RNA was extracted according to the method of Chomszinsky and Sacchi (Chomczynski, P., and Sacchi, N. (1987) Single-step method of RNA isolation by acid guanidinium thiocyanate-phenol-chloroform extraction. Anal. Biochem. 162, 156-159.), but without addition of tRNA. After ethanol precipitation, the RNA pellet was dissolved in 50 μl sterile RNase-free water. The integrity of the total RNA was verified by denaturing gel electrophoresis. The RNA was stored until use in 5 mM sodium citrate pH 5.5 at −80° C.

The cDNA pool encoding the long chain α-neurotoxins was cloned from total venom RNA of *N. kaouthia* using a two-step, nested RT-PCR protocol. About 2 μg of total venom RNA was denatured at 65° C. for 5 min in the presence of 1 mM dNTPs and Oligo(d)$T_{20}$ primer (0.5 μg; Invitrogen), then placed on ice. The reverse transcription (RT) reaction was set-up in 20 μl with RNase-free water, 15 U of cMaster™ RT enzyme (AMV RT, Eppendorf), 2 U Prime™ RNase Inhibitor (Eppendorf) and 4 μl of 5× RTplusPCR™ buffer. The RT reaction was incubated at 42° C. for 1 hour. The first subsequent PCR was carried out adding 2 μl of the RT reaction mix to a 50 μl PRC reaction mix containing 1.25 U of Taq DNA polymerase (Eppendorf), 200 μM dNTPs (Eppendorf), 1× Tuning™ Buffer (Eppendorf), 2.5 mM magnesium acetate, 0.2 μM of the universal three finger toxin forward primer (ATGAAAACTCTGCTGCTGACC) (SEQ ID NO:95) and 0.2 μM of the universal three finger toxin reverse primer (CTCAAACTACAGAACTAGCAG) (SEQ ID NO:96). After 2 min of initial template denaturation at 94° C., 35 cycles of the following temperature cycling program was carried out on an Eppendorf™ Mastercycler: 94° C.—15 s, 59° C.—30 s, 68° C.—60 s. For the second, nested PCR step the reaction of the first PCR step was diluted 1:100 with $H_2O$ after completion. Then 0.5 μl of the diluted reaction mix was used as the template in the second PCR reaction.

The second PCR was carried out under the same conditions as the first PCR, but using 0.2 μM of the specific long chain α-neurotoxin forward primer (GACTTAGGATACACCATAAG) (SEQ ID NO:97) and 0.2 μM of the specific long chain α-neurotoxin reverse primer (TTGAGTT TTGCTCTCATCCATC) (SEQ ID NO:98). The final PCR product of 300 bp in size was gel-purified for subsequent cloning using the PerfectPrep™ Gel Clean-Up Kit (Eppendorf AG, Germany). The purified PCR product was cloned directly into the pGEM-T plasmid vector (Promega, Madison, Wis.) using standard procedures for DNA fragment ligation, *E. coli* transformation, colony screening and plasmid DNA isolation known to specialist in the art. A total of 192 recombinant clones were selected for DNA sequencing to determine the exact coding sequences of long chain alpha neurotoxins from *N. kaouthia*. All identified unique long chain alpha neurotoxin sequences cloned from the venom glands of *N. kaouthia* are listed in Table 3.

TABLE 4

Amino acid sequences of the unique short and long chain α-neurotoxin mRNAs cloned from the venom glands of *N. kaouthia*. Note that in the fourth sequence below the highly conserved $5^{th}$ cysteine residue is substituted by an arginine, which abolishes the formation of the disulfate bridge at the tip of loop II critical for binding the α7-subunit in the neuronal nAChR.

| |
|---|
| Unique long-chain α-neurotoxin sequences from *N. Kaouthia* |
| IRCFITPDITSKDCPNGHVCYTKTWCDAFCSIRGKRVDLGCAATCPTVKTGVDIQCCSTDNCNPFPTRKRP (SEQ ID NO: 1) |
| IRCFITPDITSKDCPNGHVCYTKTWCDAFCSIRGKGVDLGCAATCPTVKTGVDIQCCSTDNCNPFPTRKRP (SEQ ID NO: 2) |
| IRCFITPDITSKDCPNGHVCYTKTWCDAFCSIRGKRVDLGCAATCPTVKTGVDIQCCSTDNCT (SEQ ID NO: 3) |
| IRCFITPDITSKDCPNGRVCYTKTWCDAFRSIRGKRVDLGCAATCPTVKTGVDIQCCSTDNCNPFPTRKRP (SEQ ID NO: 4) |
| Unique short-chain α-neurotoxin sequences from *N. Kaouthia* |
| LECHNQQSSQTPTTTGCSGGETNCYKKRWRDHRGYRTERGCGCPSVRNGIEINCCTTDRCNN (SEQ ID NO: 80) |
| LECHNQQSSQAPTTKTCSGETNCYKKRWRDHRGYRTERGCGCPSVRNGIEINCCTTDRCNN (SEQ ID NO: 81) |
| LECHNQQSSQAPTTKTCSGETNCYKKWWSDHRGTIIERGCGCPKVKPGVNLNCCRTDRCNN (SEQ ID NO: 82) |

TABLE 4-continued

| Amino acid sequences of the unique short and long chain α-neurotoxin mRNAs cloned from the venom glands of *N. kaouthia*. Note that in the fourth sequence below the highly conserved 5th cysteine residue is substituted by an arginine, which abolishes the formation of the disulfate bridge at the tip of loop II critical for binding the α7-subunit in the neuronal nAChR. |
|---|
| LECHNQQSSQTPTTKTCSGETNCYKKWWSDHRGTIIERGCGCPKVKPGVNLNCCRRDRCNN (SEQ ID NO: 83) |

Example 2: Culturing Cells of Fetal Human Skeletal Muscle Cells Expressing Human Muscular nAChR (α1,β1,γ,δ)

Any technique known in the art for culturing mammalian cells can be employed to culture human fetal HSkMC (pre-screened HSkMC, Cell Applications Inc., San Diego, Cat#5150-05f).

The preferred technique for growing HSkMC cells employs "Skeletal Muscle Cell Growth Medium" (Cell Applications Inc., San Diego, Cat#151-500) in an atmosphere of 90% air and 5% $CO_2$ at 37° C. following the cell supplier's recommendation.

Small volumes are grown in 35 mm dishes using an innoculum of $3\times10^5$ cells in 1.5 ml of medium. After three days the medium is changed, and optimal AChR yield is obtained on day six or seven.

For large volumes, plastic roller bottles (Falcon Labware, Becton-Dickinson, Inc., Oxnard, Calif. U.S.A.) are used. In the case of 850 $cm^2$ bottles, $3\times10^7$ cells are inoculated in 150 ml of medium; whereas, for 1750 $cm^2$ bottles, $6\times10^7$ cells are inoculated in 300 ml of medium. The medium is changed on day five, and AChR yield is optimal on days nine to ten.

Example 3: Selective Reduction and Alkylation of the 5th Disulfide Bond in Long Chain α-Cobratoxin 1 from *N. kaouthia*

For selective reduction of the 5th dilsulfide bond in loop II 1.2 mM of the toxin is incubated with 2.5 mM dithiothreitol in 0.2 M Tris buffer, pH 8.5, 1 mg/ml EDTA for 90 min at 4° C. Thereafter, 2,2'-dithiopyridine dissolved in methanol is added to a final concentration of 15 mM and incubated for 1 h at room temperature. The alkylated Cobratoxin-dithiopyridine obtained is purified by gel filtration (Bio-Gel P-2) and HPLC chromatography (Vydac C8). One skilled in the art understands that this procedure can be applied for selective reduction of any long chain α-neurotoxin that shares the common three finger fold with α-bungarotoxin and α-cobratoxin. The exemplified toxins were only chosen based on their commercial availability in purified form.

Example 4: Isolation of Acetylcholine Receptor Complexes from Cells for Binding Assays AChR are typically isolated from the cultures from six or seven 850 $cm^2$ roller bottles at a time, although much larger volumes of culture can easily be processed simultaneously. The following procedure is used routinely for the isolation of AChR from cultures of fetal human HSkMC, samples of which are available from Cell Applications Inc., San Diego, under catalogue No. 151-500.

To each 850 $cm^2$ bottle of culture on day nine or ten, after growth as described in Example II, is added 25 ml of harvest buffer (100 mM NaCl, 10 mM Na phosphate buffer, 10 mM $NaN_3$, 15 mM EDTA, 2 mM PMSF (phenylmethanesulfonylfluoride), 15 mM IAA (iodoacetic acid), and 5 mM benzamidine, pH 7.5). The bottles are then vigorously shaken until the cells come off of the plastic. Cells that remain adhered to the bottle's surface are carefully scraped off with a sterile plastic cell scraper. The buffer and cells are collected in a bottle on ice, and the roller bottles are rinsed from bottle to bottle with an additional 100 ml of harvest buffer, which is then pooled with the rest. A Polytron homogenizer is then used to disrupt the cells for 15 seconds at a speed just below that at which foaming occurs. Membranes and other particulates are collected by centrifuging the homogenate for 30 minutes at 300,000 g at 4° C. Typically, about 1.5 gm of pellet is recovered per 850 $cm^2$ bottle. The pellets are placed in four volumes of extraction buffer (10 mM Na phosphate, 5 mM EDTA, 5 mM EGTA, 5 mM IAA, 5 mM benzamidine, 2 mM PMSF, 2% Triton X-100, pH 7.5) and gently suspended with the Polytron for 15 seconds. After extraction for 30 minutes with gentle shaking at 4° C., the preparation is centrifuged as before. The supernatant containing the extracted nAChR is then aspirated, aliquoted and shock-frozen in liquid nitrogen for further storage at −80° C. The protein concentration of the nAChR extract can be determined using the BCA™ Protein Assay Kit-Reducing Agent Compatible (Pierce, Cat#3250).

Example 5: Binding Assays for Determining α-Neurotoxin Binding Specificity

The binding assay is essentially an ELISA using cellular extracts enriched in human nAChR (either neuronal or muscular type) for coating the microtiter plate wells and FITC-labeled α-bungarotoxin (Sigma-Aldrich, Cat#T9641) as a labeled tracer. The quantitative signal detected is the fluorescence of the labeled tracer measured in RF units at 525 nm on a Fluorescence Microtiter Plate Scanner. Alternatively for greater sensitivity, the FITC-labeled tracer can also be detected colometrically with a sandwich of a Monoclonal Anti-FITC antibody (Sigma-Aldrich, Cat#F5636), Anti-Mouse IgG (whole molecule)—Biotin antibody (Sigma-Aldrich, Cat#B7264) and streptavidin-alkaline phosphatase conjugate and a chemiluminescent phosphatase substrate (Sigma-Aldrich, Cat#52890; Cat#). For quantification, the fluorescence RF units are correlated to molar concentrations of the labeled tracer toxin by recording the fluorescence (or chemiluminescence) of a series of FITC-labeled α-bungarotoxin dilutions ranging from 0.1 to 20 nM prepared from a gravimetrically formulated stock with exact molar concentration. The resulting fluorescence calibration curve allows deviating molar concentration of the labeled tracer from the measured fluorescent signal. It is also used to determine the sensitivity threshold of the assay. To prepare the 96-well polystyrene microtiter plates for the ELISA assay each well is coated with a nAChR-extract diluted in PBS (2-5 nM α1). Therefore 50-150 ul of the diluted extract per well is incubated overnight at 4° C. Non-specific binding sites in the wells are blocked by a subsequent incubation with 100-150 ul per well of PBS containing 3% BSA at 4° C. for 2 hours with shaking. For each batch of the nAChR-extract the saturating tracer concentration has to be determined empirically, at which all specific toxin binding sites per well are engaged. Therefore, for each lot one plate is incubated with a dilution series of the labeled tracer toxin ranging between 1 to 10 nM and the tracer concentration is determined at which saturation of the fluorescent signal is reached (usually between 2 to 5 nM). The lowest tracer concentration at which fluorescence signal saturation is reached will be used in all wells sharing the same batch of the nAChR-extract.

In the first step of the assay serial dilutions (100-150 μl) ranging from 1 μM to 2 nM of the alkylated and non-modified, long chain neurotoxin competitors (Sigma-Aldrich; α-cobratoxin, Cat#C6903; α-bungarotoxin, Cat#T3019 are incubated in PBS buffer at RT for at least 30 minutes. After the incubation with competitor toxins, FITC-labeled α-bungarotoxin (tracer) is added to saturating concentration (equal in all wells) and incubated for another 30 minutes. Each well is rinsed 3 times with 150 ul PBS before measuring the remaining fluorescence at 525 nm. The protection constant calculated by fitting the competition data by the Hill equation corresponds to the Kd value as was shown in the prior art (6).

Example 6: Evaluation of Chemodenervation Effect a) The Hind Limb Regional Chemodenervation Assay:

Injection of the subject postsynaptic chemodenervation polypeptides into the mouse gastrocnemius muscle results in a number of effects on hind limb function. Paw paralysis is observed at lower doses and is also an early partial response to injection of higher doses of α-neurotoxin. As used herein, "complete paw paralysis" is defined as the inability of the mouse to grip with the paw. At higher doses, there occurs a further progression to more generalized compromised function of the injected limb and ultimately to complete hind limb paralysis. "Complete hind limb paralysis" is defined as the complete absence of voluntary movement of the injected limb.

Accordingly, two measures of the extent of denervation are utilized, one is complete hind limb paralysis and the other is complete paw paralysis. As used herein, partial paralysis also means paw paralysis and complete paralysis also means hind limb paralysis.

The amount of postsynaptic chemodenervation polypeptide in a given preparation is calibrated using two different units of biologic activity. The conventional calibration standard unit of activity for neurotoxins is the $LD_{50}$ in mice; 1.0 $LD_{50}$ is equivalent to 1.0 unit of activity. An alternative calibration unit is the median paralysis unit (MPU); as used herein, 1.0 MPU is that amount of α-neurotoxin which produces complete hind limb paralysis in 50% of a population of mice. The methods for determination of these units of activity are described in detail below.

(b) Determination of the Median Paralysis Unit:

Paralysis of the mouse hind limb is produced by i.m. injection of the subject polypeptides using an art-recognized method similar to that previously described by Pearce et al. (1994) 128 Toxicol. App. Pharmacology 69. Briefly, an α-neurotoxin of the present invention is injected into the gastrocnemius muscle of the hind limb of 18-22 g mice. Neurotoxic activity is assessed by evaluating the fraction of mice that show complete paralysis of the right rear hind limb. Complete paralysis is manifested as an inability of the mouse to use the right rear hind limb to support weight or to escape. Once complete paralysis occurs, the hind limb is usually held up against the body or dragged. These postures are considered cardinal signs of complete paralysis.

Five to six dilutions of α-neurotoxin are injected into 10 mice per dilution. Doses of α-neurotoxin are increased in a geometric progression by a factor of 1.25. Applying well-known statistical considerations, doses are centered on the $ED_{50}$ (median effective dose) to provide a symmetric design (Finney, D. J. (1978) Statistical Method in Biological Assay Charles Griffin & Co., London). To avoid bias, only doses of neurotoxin at which no death occurs prior to determining the $ED_{50}$ are utilized in the probit analysis. The percent paralyzed is determined at each dose of α-neurotoxin and standard probit analysis is performed on the data (Bliss, C. I. (1938) 11 Q.J. Pharm. Pharmac. 192-216) using the probit program provided with the statistical package, SPSS-X (SPSS, Inc., Chicago, Ill.). This program estimates the best line by regression analysis and the values for the intercept and slope are estimated by the maximum likelihood method. A standard Pearson chi-square goodness of fit test is used and, if this estimate is significant, a heterogeneity factor is then used in the calculation of the confidence limits. The $ED_{50}$ obtained from this type of experiment is specifically referred to herein as the median paralysis unit (MPU).

(c) Determination of the $LD_{50}$:

Samples of α-neurotoxin are diluted. Generally, 5 dilutions of α-neurotoxin and 5 or 10 mice are used per dilution. Several different series of dilutions are used and the ratio between successive doses determined. Dilutions are increased in approximately a geometric progression to achieve a symmetric design using well-known statistical methods similar to those described by Finney, D. J. (1978) Statistical Method in Biological Assay (Charles Griffin & Co., London). The diluted samples of α-neurotoxin are administered by i.p. injection to 18-22 g mice. Following injection the mice are observed for 4 days.

The percent death is determined at each dose of neurotoxin and probit analysis is performed on the data using the probit program described above. In keeping with conventional statistical practices, the 95% fudicial confidence intervals for the estimates of the $LD_{50}$ were determined using art-recognized methods similar to those described by Finney, D. J., (1971) Probit Analysis (3rd Ed.) University Press, Cambridge. Again, a Pearson chi-square goodness of fit test is used and if this estimate s significant, a heterogeneity factor is used in the calculation of the confidence limits.

Example 7: Dose-Effect Study and Comparison

A total of 50 rats are studied (10 in each of 5 groups). All animals are anesthetized with pentobarbital (60 mg/kg) given by intraperitoneal administration and maintained with supplemental doses as determined by physiological monitoring variables. A tracheotomy is performed and the rats are ventilated with room air keeping $P_{CO2}$ near 35 torr. The carotid artery is cannulated to measure blood pressure and arterial blood gases. The right jugular vein is cannulated for intravenous infusion and further drug administration. Body temperature is maintained at 36°-38° C. during the entire experiment. The sciatic nerve is exposed in the popliteal space and stimulated with train-of-four stimulation using a Digistim nerve stimulator. The tivialis anterior muscle contraction is measured by attaching the rat hind limb to an isometric force transducer to record the evoked response. Prior to administration of the postsynaptic chemodenervation polypeptide, baseline measurements of blood pressure, heart rate and muscle contraction force are measured for a five-minute period and at five minute intervals for the duration of the study.

The initial dose for analysis is based on biologically effective doses determined in mice, as described in Example 6 above. Based on the onset, maximum effect and duration of effect from the first animal studied, the dose for the next animal is either doubled or halved. If the relaxation level is maintained at a maximal level for greater than 20 minutes from this initial dose, then the subsequent dose studied is doubled. This progression continues until the dose that produced near maximal muscle relaxation is found.

Two postsynaptic chemodenervation polypeptides are studied in the initial study and compared against conventional presynaptic targeting agents. For each compound studied, the onset of muscle relaxation, duration of relaxation and an estimate of the $ED_{50}$ is determined from evoked force transducer response. Onset of relaxation is defined as the time for the evoked response to diminish to 5% of pre-drug baseline. In addition, clinical duration, defined as the time from the administration of drug until the evoked muscle response returns to 25% of its pre-drug baseline, and recovery time, defined as the time until evoked response returns to 75% of baseline, is also determined. Data are summarized for each compound. These results will show that the polypeptides are biologically active at the neuromuscular junction producing skeletal muscle paralysis that mimics the response seen with conventional non-depolarizing neuromuscular blocking agents given during anesthesia.

Example 8: Evaluation of Chemodenervation Effect of α-Neurotoxin In Vivo

Experiments are carried out on cats of either sex anaesthetized with a mixture of α-chloralose (80 mg kg-.sup.1) and pentobarbitone sodium (5 mg kg-.sup.1) injected intraperitoneally. Animals are ventilated with room air at the rate of 26 breaths per minute using a tidal volume of 13 ml kg-.sup.1. The left and right hind limbs are immobilized by drills inserted into the ankle and knee joints. The contractile responses of the tibialis anterior and soleus muscles to stimulation of the sciatic nerve are recorded. The sciatic nerve is stimulated at rates from 0.1 Hz-200 Hz using rectangular pulses of 0.2 ms duration and of a strength greater than that required to produce a maximal twitch. Arterial blood pressure is recorded from the carotid artery using a Statham PC45 pressure transducer. The blood pressure pulse is used to trigger a cardiotachograph to display the heart rate. In some experiments both vagus nerves are ligated and, at 100 s intervals, the right vagus nerve is stimulated with 10 s duration trains at a frequency of 2-5 Hz and with pulses of 0.5 ms duration and strength greater than that required to produce a maximal reduction in heart rate. Contractions of the nictitating membrane are evoked every 100 s by preganglionic stimulation of the cervical sympathetic nerve with 10 s duration trains at a frequency of 5 Hz and of strength to produce maximal contractions of the nictitating membrane. Contractile responses of muscles are recorded using Grass FT03C and FT10C force displacement transducers. All responses are displayed on a Grass model 5 ink writing oscillograph.

In assessing the efficacy of the subject postsynaptically targeted polypeptides, responses from both tibialis anterior muscles are recorded; the injected muscle and the contralateral muscle which serves as a control for assessment of spillover. The subject postsynaptically targeted polypeptides are highly specific for the muscular acetylcholine receptors at the neuromuscular junction. It is therefore expected that no effects attributable to the toxins will be observed on responses of tissues to autonomic stimulation. A lack of spillover into the general circulation is also expected to be a contributing factor to the lack of autonomic actions.

All references and patents cited herein are expressly incorporated herein in their entirety by reference.

We claim:

1. A cosmetic composition comprising a recombinant α-neurotoxin lacking a fifth disulfide bond in loop II of the three finger fold and a transdermal chaperone, wherein said α-neurotoxin exhibits a $K_D$ for the alpha-1-containing, human muscular nAChR that is at least 100-fold less than it's $K_D$ for any of the neuronal nAChR comprising α7nAChR, α3nAChR, α4nAChR, and α2nAChR.

2. The cosmetic composition according to claim 1, wherein said cosmetic composition comprises a single α-neurotoxin species.

3. The cosmetic composition according to claim 1, wherein said composition comprises a defined mixture of two or more α-neurotoxin species.

4. The cosmetic composition according to claim 1, wherein said transdermal chaperone comprises a transdermal peptide.

5. The cosmetic composition according to claim 4, wherein said transdermal peptide comprises the sequence ACSSSPSKHCG (SEQ ID NO:94).

6. The cosmetic composition according to claim 1, wherein said α-neurotoxin is a native short-chain α-neurotoxin.

7. The cosmetic composition according to claim 1, wherein said α-neurotoxin is a native long-chain α-neurotoxin lacking a fifth disulfide bond in loop II of the three finger fold.

8. The cosmetic composition according to claim 1, wherein said α-neurotoxin comprises a modified long-chain α-neurotoxin lacking a fifth disulfide bond in loop II of the three finger fold.

* * * * *

SEQUENCE LISTING

```
<160> NUMBER OF SEQ ID NOS: 98

<210> SEQ ID NO 1
<211> LENGTH: 71
<212> TYPE: PRT
<213> ORGANISM: Naja kaouthia

<400> SEQUENCE: 1

Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Ala Phe Cys Ser Ile
            20                  25                  30

Arg Gly Lys Arg Val Asp Leu Gly Cys Ala Ala Thr Cys Pro Thr Val
        35                  40                  45

Lys Thr Gly Val Asp Ile Gln Cys Cys Ser Thr Asp Asn Cys Asn Pro
    50                  55                  60

Phe Pro Thr Arg Lys Arg Pro
65                  70


<210> SEQ ID NO 2
<211> LENGTH: 71
<212> TYPE: PRT
```

<213> ORGANISM: Naja kaouthia

<400> SEQUENCE: 2

```
Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Ala Phe Cys Ser Ile
            20                  25                  30

Arg Gly Lys Gly Val Asp Leu Gly Cys Ala Ala Thr Cys Pro Thr Val
        35                  40                  45

Lys Thr Gly Val Asp Ile Gln Cys Cys Ser Thr Asp Asn Cys Asn Pro
    50                  55                  60

Phe Pro Thr Arg Lys Arg Pro
65                  70
```

<210> SEQ ID NO 3
<211> LENGTH: 63
<212> TYPE: PRT
<213> ORGANISM: Naja kaouthia

<400> SEQUENCE: 3

```
Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Ala Phe Cys Ser Ile
            20                  25                  30

Arg Gly Lys Arg Val Asp Leu Gly Cys Ala Ala Thr Cys Pro Thr Val
        35                  40                  45

Lys Thr Gly Val Asp Ile Gln Cys Cys Ser Thr Asp Asn Cys Thr
    50                  55                  60
```

<210> SEQ ID NO 4
<211> LENGTH: 71
<212> TYPE: PRT
<213> ORGANISM: Naja kaouthia

<400> SEQUENCE: 4

```
Ile Arg Cys Phe Ile Thr Pro Asp Ile Thr Ser Lys Asp Cys Pro Asn
 1               5                  10                  15

Gly Arg Val Cys Tyr Thr Lys Thr Trp Cys Asp Ala Phe Arg Ser Ile
            20                  25                  30

Arg Gly Lys Arg Val Asp Leu Gly Cys Ala Ala Thr Cys Pro Thr Val
        35                  40                  45

Lys Thr Gly Val Asp Ile Gln Cys Cys Ser Thr Asp Asn Cys Asn Pro
    50                  55                  60

Phe Pro Thr Arg Lys Arg Pro
65                  70
```

<210> SEQ ID NO 5
<211> LENGTH: 71
<212> TYPE: PRT
<213> ORGANISM: Naja naja

<400> SEQUENCE: 5

```
Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Ala Phe Cys Ser Ile
            20                  25                  30

Arg Gly Lys Arg Val Asp Leu Gly Cys Ala Ala Thr Cys Pro Thr Val
        35                  40                  45
```

-continued

```
Lys Thr Gly Val Asp Ile Gln Cys Cys Ser Thr Asp Asp Cys Asp Pro
    50                  55                  60

Phe Pro Thr Arg Lys Arg Pro
65                  70


<210> SEQ ID NO 6
<211> LENGTH: 71
<212> TYPE: PRT
<213> ORGANISM: Naja naja

<400> SEQUENCE: 6

Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Gly Phe Cys Ser Ile
            20                  25                  30

Arg Gly Lys Arg Val Asp Leu Gly Cys Ala Ala Thr Cys Pro Thr Val
        35                  40                  45

Arg Thr Gly Val Asp Ile Gln Cys Cys Ser Thr Asp Asp Cys Asp Pro
    50                  55                  60

Phe Pro Thr Arg Lys Arg Pro
65                  70


<210> SEQ ID NO 7
<211> LENGTH: 71
<212> TYPE: PRT
<213> ORGANISM: Naja naja

<400> SEQUENCE: 7

Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Gly Phe Cys Arg Ile
            20                  25                  30

Arg Gly Glu Arg Val Asp Leu Gly Cys Ala Ala Thr Cys Pro Thr Val
        35                  40                  45

Lys Thr Gly Val Asp Ile Gln Cys Cys Ser Thr Asp Asp Cys Asp Pro
    50                  55                  60

Phe Pro Thr Arg Lys Arg Pro
65                  70


<210> SEQ ID NO 8
<211> LENGTH: 71
<212> TYPE: PRT
<213> ORGANISM: Naja naja

<400> SEQUENCE: 8

Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Gly Phe Cys Ser Arg
            20                  25                  30

Arg Gly Glu Arg Val Asp Leu Gly Cys Ala Ala Thr Cys Pro Thr Val
        35                  40                  45

Lys Thr Gly Val Asp Ile Gln Cys Cys Ser Thr Asp Asp Cys Asp Pro
    50                  55                  60

Phe Pro Thr Arg Lys Arg Pro
65                  70


<210> SEQ ID NO 9
<211> LENGTH: 71
<212> TYPE: PRT
```

<213> ORGANISM: Naja naja

<400> SEQUENCE: 9

```
Ile Arg Cys Phe Ile Thr Pro Asp Ile Thr Ser Lys Asp Cys Pro Asn
 1               5                  10                  15

Gly His Val Cys Tyr Thr Lys Thr Trp Cys Asp Gly Phe Cys Ser Ser
            20                  25                  30

Arg Gly Lys Arg Val Asp Leu Gly Cys Ala Ala Thr Cys Pro Thr Val
        35                  40                  45

Arg Thr Gly Val Asp Ile Gln Cys Cys Ser Thr Asp Asp Cys Asp Pro
    50                  55                  60

Phe Pro Thr Arg Lys Arg Pro
65                  70
```

<210> SEQ ID NO 10
<211> LENGTH: 69
<212> TYPE: PRT
<213> ORGANISM: Naja sputatrix

<400> SEQUENCE: 10

```
Ile Arg Cys Phe Ile Thr Pro Asp Val Thr Ser Thr Asp Cys Pro Asn
 1               5                  10                  15

Gly His Val Cys Tyr Thr Lys Thr Trp Cys Asp Gly Phe Cys Ser Ser
            20                  25                  30

Arg Gly Arg Arg Val Glu Leu Gly Cys Ala Ala Thr Cys Pro Thr Val
        35                  40                  45

Lys Pro Gly Val Asp Ile Gln Cys Cys Ser Thr Asp Asn Cys Asn Pro
    50                  55                  60

Phe Pro Thr Arg Pro
65
```

<210> SEQ ID NO 11
<211> LENGTH: 72
<212> TYPE: PRT
<213> ORGANISM: Naja haje haje

<400> SEQUENCE: 11

```
Ile Arg Cys Phe Ile Thr Pro Asp Val Thr Ser Gln Ala Cys Pro Asp
 1               5                  10                  15

Gly Gln Asn Ile Cys Tyr Thr Lys Thr Trp Cys Asp Asn Phe Cys Gly
            20                  25                  30

Met Arg Gly Lys Arg Val Asp Leu Gly Cys Ala Ala Thr Cys Pro Thr
        35                  40                  45

Val Lys Pro Gly Val Asp Ile Lys Cys Cys Ser Thr Asp Asn Cys Asn
    50                  55                  60

Pro Phe Pro Thr Arg Glu Arg Ser
65                  70
```

<210> SEQ ID NO 12
<211> LENGTH: 71
<212> TYPE: PRT
<213> ORGANISM: Naja haje haje

<400> SEQUENCE: 12

```
Ile Arg Cys Phe Ile Thr Pro Asp Val Thr Ser Gln Ala Cys Pro Asp
 1               5                  10                  15

Gly His Val Cys Tyr Thr Lys Met Trp Cys Asp Asn Phe Cys Gly Met
            20                  25                  30
```

-continued

```
Arg Gly Lys Arg Val Asp Leu Gly Cys Ala Ala Thr Cys Pro Thr Val
        35                  40                  45

Lys Pro Gly Val Asp Ile Lys Cys Cys Ser Thr Asp Asn Cys Asn Pro
    50                  55                  60

Phe Pro Thr Arg Lys Arg Ser
65                  70


<210> SEQ ID NO 13
<211> LENGTH: 73
<212> TYPE: PRT
<213> ORGANISM: Naja oxiana

<400> SEQUENCE: 13

Ile Thr Cys Tyr Lys Thr Pro Ile Pro Ile Thr Ser Glu Thr Cys Ala
 1               5                  10                  15

Pro Gly Gln Asn Leu Cys Tyr Thr Lys Thr Trp Cys Asp Ala Trp Cys
            20                  25                  30

Gly Ser Arg Gly Lys Val Ile Glu Leu Gly Cys Ala Ala Thr Cys Pro
        35                  40                  45

Thr Val Glu Ser Tyr Gln Asp Ile Lys Cys Cys Ser Thr Asp Asp Cys
    50                  55                  60

Asn Pro His Pro Lys Gln Lys Arg Pro
65                  70


<210> SEQ ID NO 14
<211> LENGTH: 71
<212> TYPE: PRT
<213> ORGANISM: Naja nivea

<400> SEQUENCE: 14

Ile Arg Cys Phe Ile Thr Pro Asp Val Thr Ser Gln Ala Cys Pro Asp
 1               5                  10                  15

Gly His Val Cys Tyr Thr Lys Met Trp Cys Asp Asn Phe Cys Gly Met
            20                  25                  30

Arg Gly Lys Arg Val Asp Leu Gly Cys Ala Ala Thr Cys Pro Lys Val
        35                  40                  45

Lys Pro Gly Val Asn Ile Lys Cys Cys Ser Arg Asp Asn Cys Asn Pro
    50                  55                  60

Phe Pro Thr Arg Lys Arg Ser
65                  70


<210> SEQ ID NO 15
<211> LENGTH: 71
<212> TYPE: PRT
<213> ORGANISM: Naja melanoleuca

<400> SEQUENCE: 15

Ile Arg Cys Phe Ile Thr Pro Asp Val Thr Ser Gln Ile Cys Ala Asp
 1               5                  10                  15

Gly His Val Cys Tyr Thr Lys Thr Trp Cys Asp Asn Phe Cys Ala Ser
            20                  25                  30

Arg Gly Lys Arg Val Asp Leu Gly Cys Ala Ala Thr Cys Pro Thr Val
        35                  40                  45

Lys Pro Gly Val Asn Ile Lys Cys Cys Ser Thr Asp Asn Cys Asn Pro
    50                  55                  60

Phe Pro Thr Arg Asn Arg Pro
65                  70
```

-continued

<210> SEQ ID NO 16
<211> LENGTH: 71
<212> TYPE: PRT
<213> ORGANISM: Naja melanoleuca

<400> SEQUENCE: 16

```
Lys Arg Cys Tyr Arg Thr Pro Asp Leu Lys Ser Gln Thr Cys Pro Pro
 1               5                  10                  15

Gly Glu Asp Leu Cys Tyr Thr Lys Lys Trp Cys Ala Asp Trp Cys Thr
            20                  25                  30

Ser Arg Gly Lys Val Ile Glu Leu Gly Cys Val Ala Thr Cys Pro Lys
        35                  40                  45

Val Lys Pro Tyr Glu Gln Ile Thr Cys Cys Ser Thr Asp Asn Cys Asn
    50                  55                  60

Pro His Pro Lys Met Lys Pro
65                  70
```

<210> SEQ ID NO 17
<211> LENGTH: 73
<212> TYPE: PRT
<213> ORGANISM: Ophiophagus hannah

<400> SEQUENCE: 17

```
Thr Lys Cys Tyr Val Thr Pro Asp Val Lys Ser Glu Thr Cys Pro Ala
 1               5                  10                  15

Gly Gln Asp Ile Cys Tyr Thr Glu Thr Trp Cys Asp Ala Trp Cys Thr
            20                  25                  30

Ser Arg Gly Lys Arg Val Asp Leu Gly Cys Ala Ala Thr Cys Pro Ile
        35                  40                  45

Val Lys Pro Gly Val Glu Ile Lys Cys Cys Ser Thr Asp Asn Cys Asn
    50                  55                  60

Pro Phe Pro Thr Trp Arg Lys Arg Pro
65                  70
```

<210> SEQ ID NO 18
<211> LENGTH: 73
<212> TYPE: PRT
<213> ORGANISM: Ophiophagus hannah

<400> SEQUENCE: 18

```
Thr Lys Cys Tyr Val Thr Pro Asp Ala Thr Ser Gln Thr Cys Pro Asp
 1               5                  10                  15

Gly Gln Asp Ile Cys Tyr Thr Lys Thr Trp Cys Asp Gly Phe Cys Ser
            20                  25                  30

Ser Arg Gly Lys Arg Ile Asp Leu Gly Cys Ala Ala Thr Cys Pro Lys
        35                  40                  45

Val Lys Pro Gly Val Asp Ile Lys Cys Cys Ser Thr Asp Asn Cys Asn
    50                  55                  60

Pro Phe Pro Thr Trp Lys Arg Lys His
65                  70
```

<210> SEQ ID NO 19
<211> LENGTH: 73
<212> TYPE: PRT
<213> ORGANISM: Ophiophagus Hannah

<400> SEQUENCE: 19

```
Thr Lys Cys Tyr Val Thr Pro Asp Val Lys Ser Glu Thr Cys Pro Ala
 1               5                  10                  15
```

```
Gly Gln Asp Leu Cys Tyr Thr Glu Thr Trp Cys Val Ala Trp Cys Thr
            20                  25                  30

Val Arg Gly Lys Arg Val Ser Leu Thr Cys Ala Ala Ile Cys Pro Ile
        35                  40                  45

Val Pro Pro Lys Val Ser Ile Lys Cys Cys Ser Thr Asp Ala Cys Gly
    50                  55                  60

Pro Phe Pro Thr Trp Pro Asn Val Arg
65                  70


<210> SEQ ID NO 20
<211> LENGTH: 72
<212> TYPE: PRT
<213> ORGANISM: Ophiophagus Hannah

<400> SEQUENCE: 20

Thr Lys Cys Tyr Lys Thr Gly Asp Arg Ile Ile Ser Glu Ala Cys Pro
 1               5                  10                  15

Pro Gly Gln Asp Leu Cys Tyr Met Lys Thr Trp Cys Asp Val Phe Cys
            20                  25                  30

Gly Thr Arg Gly Arg Val Ile Glu Leu Gly Cys Thr Ala Thr Cys Pro
        35                  40                  45

Thr Val Lys Pro His Glu Gln Ile Thr Cys Cys Ser Thr Asp Asn Cys
    50                  55                  60

Asn Pro His Pro Lys Met Lys Gln
65                  70


<210> SEQ ID NO 21
<211> LENGTH: 72
<212> TYPE: PRT
<213> ORGANISM: Ophiophagus Hannah

<400> SEQUENCE: 21

Thr Lys Cys Tyr Lys Thr Gly Asp Arg Ile Ile Ser Glu Ala Cys Pro
 1               5                  10                  15

Pro Gly Gln Asp Leu Cys Tyr Met Lys Thr Trp Cys Asp Val Phe Cys
            20                  25                  30

Gly Thr Arg Gly Arg Val Ile Glu Leu Gly Cys Thr Ala Thr Cys Pro
        35                  40                  45

Thr Val Lys Pro His Glu Gln Ile Thr Cys Cys Ser Thr Asp Asn Cys
    50                  55                  60

Asp Pro His His Lys Met Leu Gln
65                  70


<210> SEQ ID NO 22
<211> LENGTH: 70
<212> TYPE: PRT
<213> ORGANISM: Ophiophagus Hannah

<400> SEQUENCE: 22

Leu Ile Cys Phe Ile Ser Ser His Asp Ser Val Thr Cys Ala Pro Gly
 1               5                  10                  15

Glu Asn Val Cys Phe Leu Lys Ser Trp Cys Asp Ala Trp Cys Gly Ser
            20                  25                  30

Arg Gly Lys Lys Leu Ser Phe Gly Cys Ala Ala Thr Cys Pro Lys Val
        35                  40                  45

Asn Pro Gly Ile Asp Ile Glu Cys Cys Ser Thr Asp Asn Cys Asn Pro
    50                  55                  60

His Pro Lys Leu Arg Pro
```

65 70

<210> SEQ ID NO 23
<211> LENGTH: 72
<212> TYPE: PRT
<213> ORGANISM: Ophiophagus Hannah

<400> SEQUENCE: 23

Thr Lys Cys Tyr Val Thr Pro Asp Val Lys Ser Glu Thr Cys Pro Ala
1 5 10 15

Gly Gln Asp Ile Cys Tyr Thr Glu Thr Trp Cys Asp Ala Trp Cys Thr
20 25 30

Ser Arg Gly Lys Arg Val Asn Leu Gly Cys Ala Ala Thr Cys Pro Ile
35 40 45

Val Lys Pro Gly Val Glu Ile Lys Cys Cys Ser Thr Asp Asn Cys Asn
50 55 60

Pro Phe Pro Thr Arg Lys Arg Pro
65 70

<210> SEQ ID NO 24
<211> LENGTH: 72
<212> TYPE: PRT
<213> ORGANISM: Ophiophagus Hannah

<400> SEQUENCE: 24

Thr Lys Cys Tyr Val Thr Pro Asp Ala Thr Ser Gln Thr Cys Pro Asp
1 5 10 15

Gly Glu Asn Ile Cys Tyr Thr Lys Ser Trp Cys Asp Val Phe Cys Ser
20 25 30

Ser Arg Gly Lys Arg Ile Asp Leu Gly Cys Ala Ala Thr Cys Pro Lys
35 40 45

Val Lys Pro Gly Val Asp Ile Lys Cys Cys Ser Thr Asp Asn Cys Asn
50 55 60

Pro Phe Thr Pro Trp Lys Arg His
65 70

<210> SEQ ID NO 25
<211> LENGTH: 70
<212> TYPE: PRT
<213> ORGANISM: Ophiophagus Hannah

<400> SEQUENCE: 25

Thr Lys Cys Tyr Ile Thr Pro Asp Val Lys Ser Glu Thr Cys Pro Asp
1 5 10 15

Gly Glu Asn Ile Cys Tyr Thr Lys Thr Trp Cys Asp Val Trp Cys Gly
20 25 30

Ser Arg Gly Arg Arg Val Asp Leu Gly Cys Ala Ala Thr Cys Pro Ile
35 40 45

Val Lys Pro Gly Val Asn Ile Asn Cys Cys Ser Thr Asp Asn Cys Asn
50 55 60

Pro Phe Pro Lys Arg Ser
65 70

<210> SEQ ID NO 26
<211> LENGTH: 70
<212> TYPE: PRT
<213> ORGANISM: Ophiophagus Hannah

<400> SEQUENCE: 26

```
Thr Lys Cys Tyr Val Thr Pro Asp Val Thr Ser Gln Thr Cys Pro Asp
 1               5                  10                  15

Gly Gln Asn Ile Cys Tyr Thr Glu Thr Trp Cys Asp Ala Trp Cys Gly
            20                  25                  30

Ser Arg Gly Lys Arg Val Asn Leu Gly Cys Ala Ala Thr Cys Pro Lys
        35                  40                  45

Val Asn Pro Gly Val Asp Ile Ile Cys Cys Ser Thr Asp Asn Cys Asn
    50                  55                  60

Pro Phe Pro Lys Arg Ser
65                  70


<210> SEQ ID NO 27
<211> LENGTH: 72
<212> TYPE: PRT
<213> ORGANISM: Ophiophagus Hannah

<400> SEQUENCE: 27

Thr Lys Cys Tyr Val Thr Pro Asp Val Lys Ser Glu Thr Cys Pro Asp
 1               5                  10                  15

Gly Glu Asn Ile Cys Tyr Thr Lys Ser Trp Cys Glu Val Phe Cys Thr
            20                  25                  30

Ser Arg Gly Lys Arg Ile Asp Leu Gly Arg Ala Ala Thr Cys Pro Lys
        35                  40                  45

Val Lys Pro Gly Val Asp Ile Lys Cys Cys Ser Thr Asp Asn Cys Asn
    50                  55                  60

Pro Phe Thr Pro Trp Lys Arg His
65                  70


<210> SEQ ID NO 28
<211> LENGTH: 72
<212> TYPE: PRT
<213> ORGANISM: Ophiophagus Hannah

<400> SEQUENCE: 28

Thr Lys Cys Tyr Ile Thr Pro Asp Val Lys Ser Glu Thr Cys Pro Asp
 1               5                  10                  15

Gly Glu Asn Ile Cys Tyr Thr Lys Ser Trp Cys Asp Val Phe Cys Thr
            20                  25                  30

Ser Arg Gly Lys Arg Ile Asp Leu Gly Cys Ala Ala Thr Cys Pro Lys
        35                  40                  45

Val Lys Pro Gly Val Asp Ile Lys Cys Cys Ser Thr Asp Asn Cys Asn
    50                  55                  60

Pro Phe Thr Pro Trp Lys Arg His
65                  70


<210> SEQ ID NO 29
<211> LENGTH: 70
<212> TYPE: PRT
<213> ORGANISM: Ophiophagus Hannah

<400> SEQUENCE: 29

Leu Ile Cys Phe Ile Ser Pro His Asp Ser Val Thr Cys Ala Pro Gly
 1               5                  10                  15

Glu Asn Val Cys Phe Leu Lys Ser Trp Cys Asp Ala Trp Cys Gly Ser
            20                  25                  30

Arg Gly Lys Lys Leu Ser Phe Gly Cys Ala Ala Thr Cys Pro Lys Val
        35                  40                  45

Asn Pro Gly Ile Asp Ile Glu Cys Cys Ser Thr Asp Asn Cys Asn Pro
```

```
    50                  55                  60

His Pro Lys Leu Arg Pro
65                  70


<210> SEQ ID NO 30
<211> LENGTH: 70
<212> TYPE: PRT
<213> ORGANISM: Ophiophagus Hannah

<400> SEQUENCE: 30

Leu Ile Cys Phe Ile Ser Ser His Asp Ser Val Thr Cys Ala Pro Gly
 1               5                  10                  15

Glu Asn Val Cys Phe Leu Lys Ser Trp Cys Asp Ala Trp Cys Gly Ser
            20                  25                  30

Arg Gly Lys Lys Leu Ser Phe Gly Cys Ala Ala Thr Cys Pro Lys Val
        35                  40                  45

Asn Pro Gly Ile Asp Ile Glu Cys Cys Ser Thr Asp Asn Cys Asn Pro
    50                  55                  60

His Pro Lys Leu Arg Pro
65                  70


<210> SEQ ID NO 31
<211> LENGTH: 70
<212> TYPE: PRT
<213> ORGANISM: Ophiophagus Hannah

<400> SEQUENCE: 31

Arg Ile Cys His Lys Ser Ser Phe Ile Ser Glu Thr Cys Pro Asp Gly
 1               5                  10                  15

Gln Asn Leu Cys Tyr Leu Lys Ser Trp Cys Asp Ile Phe Cys Gly Ser
            20                  25                  30

Arg Gly Glu Arg Leu Glu Phe Gly Cys Ala Ala Thr Cys Pro Glu Val
        35                  40                  45

Lys Pro Gly Val Asn Ile Glu Cys Cys Ser Thr Asp Asn Cys Asn Pro
    50                  55                  60

His Pro Lys Leu Arg Pro
65                  70


<210> SEQ ID NO 32
<211> LENGTH: 73
<212> TYPE: PRT
<213> ORGANISM: Ophiophagus Hannah

<400> SEQUENCE: 32

Thr Lys Cys Tyr Lys Thr Gly Glu Arg Ile Ile Ser Glu Thr Cys Pro
 1               5                  10                  15

Pro Gly Gln Asp Leu Cys Tyr Met Lys Thr Trp Cys Asp Val Phe Cys
            20                  25                  30

Gly Ser Arg Gly Arg Val Ile Glu Leu Gly Cys Thr Ala Thr Cys Pro
        35                  40                  45

Thr Val Lys Pro His Glu Gln Ile Thr Cys Cys Ser Thr Asp Asn Cys
    50                  55                  60

Asn Pro His Pro Lys Met Lys Gln Arg
65                  70


<210> SEQ ID NO 33
<211> LENGTH: 73
<212> TYPE: PRT
<213> ORGANISM: Ophiophagus Hannah
```

<400> SEQUENCE: 33

```
Thr Lys Cys Tyr Lys Thr Gly Glu Arg Ile Ile Ser Glu Thr Cys Pro
 1               5                  10                  15

Pro Gly Gln Asp Leu Cys Tyr Met Lys Thr Trp Cys Asp Val Phe Cys
            20                  25                  30

Gly Ser Arg Gly Arg Val Ile Glu Leu Gly Cys Thr Ala Thr Cys Pro
        35                  40                  45

Thr Val Lys His His Glu Gln Ile Thr Cys Cys Ser Thr Asp Asn Cys
    50                  55                  60

Asn Pro His Pro Lys Met Lys Gln Arg
65                  70
```

<210> SEQ ID NO 34
<211> LENGTH: 73
<212> TYPE: PRT
<213> ORGANISM: Ophiophagus Hannah

<400> SEQUENCE: 34

```
Thr Lys Cys Tyr Lys Thr Gly Glu Arg Ile Ile Ser Glu Thr Cys Pro
 1               5                  10                  15

Pro Gly Gln Asp Leu Cys Tyr Met Lys Thr Trp Cys Asp Val Phe Cys
            20                  25                  30

Gly Ser Arg Gly Arg Val Val Glu Leu Gly Cys Thr Ala Thr Cys Pro
        35                  40                  45

Thr Val Lys Pro His Glu Gln Ile Thr Cys Cys Ser Thr Asp Asn Cys
    50                  55                  60

Asn Pro His Pro Lys Met Lys Gln Arg
65                  70
```

<210> SEQ ID NO 35
<211> LENGTH: 73
<212> TYPE: PRT
<213> ORGANISM: Ophiophagus Hannah

<400> SEQUENCE: 35

```
Leu Thr Asn Ala Pro Asp Ser Trp Ser Ser Arg Arg Thr Cys Leu Cys
 1               5                  10                  15

Pro Ala Trp Val Pro Leu Arg Ser Arg Pro Val Ala Gly His Ser Lys
            20                  25                  30

Gln Cys Gly Ser Arg Gly Arg Arg Val Asp Leu Gly Cys Ala Ala Thr
        35                  40                  45

Cys Pro Ile Val Lys Pro Gly Val Asn Ile Asn Cys Cys Ser Thr Asp
    50                  55                  60

Asn Cys Asn Pro Phe Pro Lys Arg Ser
65                  70
```

<210> SEQ ID NO 36
<211> LENGTH: 71
<212> TYPE: PRT
<213> ORGANISM: Pseudonaja textilis

<400> SEQUENCE: 36

```
Arg Thr Cys Phe Ile Thr Pro Asp Val Lys Ser Lys Pro Cys Pro Pro
 1               5                  10                  15

Gly Gln Glu Val Cys Tyr Thr Glu Thr Trp Cys Asp Gly Phe Cys Gly
            20                  25                  30

Ile Arg Gly Lys Arg Val Glu Leu Gly Cys Ala Ala Thr Cys Pro Thr
```

```
        35                  40                  45

Pro Lys Lys Thr Gly Ile Asp Ile Gln Cys Cys Ser Thr Asp Asp Cys
    50                  55                  60

Asn Thr Phe Pro Leu Arg Pro
65                  70


<210> SEQ ID NO 37
<211> LENGTH: 82
<212> TYPE: PRT
<213> ORGANISM: Pseudonaja textilis

<400> SEQUENCE: 37

Arg Thr Cys Phe Ile Thr Pro Asp Val Lys Ser Lys Pro Cys Pro Pro
 1               5                  10                  15

Gly Gln Glu Val Cys Tyr Thr Lys Thr Trp Cys Asp Gly Phe Cys Gly
            20                  25                  30

Ile Arg Gly Lys Arg Val Asp Leu Gly Cys Ala Ala Thr Cys Pro Thr
        35                  40                  45

Pro Lys Lys Thr Gly Ile Asp Ile Ile Cys Cys Ser Thr Asp Asp Cys
    50                  55                  60

Asn Thr Phe Pro Leu Arg Pro Arg Gly Arg Leu Ser Ser Ile Lys Asp
65                  70                  75                  80

His Pro


<210> SEQ ID NO 38
<211> LENGTH: 73
<212> TYPE: PRT
<213> ORGANISM: Dendroaspis viridis

<400> SEQUENCE: 38

Arg Thr Cys Tyr Lys Thr Pro Ser Val Lys Pro Glu Thr Cys Pro His
 1               5                  10                  15

Gly Glu Asn Ile Cys Tyr Thr Glu Thr Trp Cys Asp Ala Trp Cys Ser
            20                  25                  30

Gln Arg Gly Lys Arg Val Glu Leu Gly Cys Ala Ala Thr Cys Pro Lys
        35                  40                  45

Val Lys Ala Gly Val Gly Ile Lys Cys Cys Ser Thr Asp Asn Cys Asn
    50                  55                  60

Pro Phe Pro Val Trp Asn Pro Arg Gly
65                  70


<210> SEQ ID NO 39
<211> LENGTH: 72
<212> TYPE: PRT
<213> ORGANISM: Dendroaspis jamesoni

<400> SEQUENCE: 39

Arg Thr Cys Tyr Lys Thr Tyr Ser Asp Lys Ser Lys Thr Cys Pro Arg
 1               5                  10                  15

Gly Glu Asp Ile Cys Tyr Thr Lys Thr Trp Cys Asp Gly Phe Cys Ser
            20                  25                  30

Gln Arg Gly Lys Arg Val Glu Leu Gly Cys Ala Ala Thr Cys Pro Lys
        35                  40                  45

Val Lys Thr Gly Val Glu Ile Lys Cys Cys Ser Thr Asp Tyr Cys Asn
    50                  55                  60

Pro Phe Pro Val Trp Asn Pro Arg
65                  70
```

```
<210> SEQ ID NO 40
<211> LENGTH: 72
<212> TYPE: PRT
<213> ORGANISM: Dendroaspis viridis

<400> SEQUENCE: 40

Arg Thr Cys Tyr Lys Thr Pro Ser Val Lys Pro Glu Thr Cys Pro His
 1               5                  10                  15

Gly Glu Asn Ile Cys Tyr Thr Glu Thr Trp Cys Asp Ala Trp Cys Ser
            20                  25                  30

Gln Arg Gly Lys Arg Glu Glu Leu Gly Cys Ala Ala Thr Cys Pro Lys
        35                  40                  45

Val Lys Ala Gly Val Gly Ile Lys Cys Cys Ser Thr Asp Asn Cys Asp
    50                  55                  60

Pro Phe Pro Val Lys Asn Pro Arg
65                  70


<210> SEQ ID NO 41
<211> LENGTH: 72
<212> TYPE: PRT
<213> ORGANISM: Dendroaspis viridis

<400> SEQUENCE: 41

Arg Thr Cys Tyr Lys Thr Pro Ser Val Lys Pro Glu Thr Cys Pro His
 1               5                  10                  15

Gly Glu Asn Ile Cys Tyr Thr Glu Thr Trp Cys Asp Ala Trp Cys Ser
            20                  25                  30

Gln Arg Gly Lys Arg Val Glu Leu Gly Cys Ala Ala Thr Cys Pro Lys
        35                  40                  45

Val Lys Ala Gly Val Gly Ile Lys Cys Cys Ser Thr Asp Asn Cys Asn
    50                  55                  60

Pro Phe Pro Val Trp Asn Pro Arg
65                  70


<210> SEQ ID NO 42
<211> LENGTH: 72
<212> TYPE: PRT
<213> ORGANISM: Dendroaspis polylepis

<400> SEQUENCE: 42

Arg Thr Cys Asn Lys Thr Phe Ser Asp Gln Ser Lys Ile Cys Pro Pro
 1               5                  10                  15

Gly Glu Asn Ile Cys Tyr Thr Lys Thr Trp Cys Asp Ala Trp Cys Ser
            20                  25                  30

Gln Arg Gly Lys Arg Val Glu Leu Gly Cys Ala Ala Thr Cys Pro Lys
        35                  40                  45

Val Lys Ala Gly Val Glu Ile Lys Cys Cys Ser Thr Asp Asp Cys Asp
    50                  55                  60

Lys Phe Gln Phe Gly Lys Pro Arg
65                  70


<210> SEQ ID NO 43
<211> LENGTH: 72
<212> TYPE: PRT
<213> ORGANISM: Dendroaspis polylepis

<400> SEQUENCE: 43

Arg Thr Cys Asn Lys Thr Pro Ser Asp Gln Ser Lys Ile Cys Pro Pro
 1               5                  10                  15
```

-continued

```
Gly Glu Asn Ile Cys Tyr Thr Lys Thr Trp Cys Asp Ala Trp Cys Ser
            20                  25                  30

Gln Arg Gly Lys Ile Val Glu Leu Gly Cys Ala Ala Thr Cys Pro Lys
        35                  40                  45

Val Lys Ala Gly Val Glu Ile Lys Cys Cys Ser Thr Asp Asn Cys Asn
    50                  55                  60

Lys Phe Lys Phe Gly Lys Pro Arg
65                  70


<210> SEQ ID NO 44
<211> LENGTH: 72
<212> TYPE: PRT
<213> ORGANISM: Dendroaspis polylepis

<400> SEQUENCE: 44

Arg Thr Cys Asn Lys Thr Phe Ser Asp Gln Ser Lys Ile Cys Pro Pro
 1               5                  10                  15

Gly Glu Asn Ile Cys Tyr Thr Lys Thr Trp Cys Asp Ala Trp Cys Ser
            20                  25                  30

Arg Arg Gly Lys Ile Val Glu Leu Gly Cys Ala Ala Thr Cys Pro Lys
        35                  40                  45

Val Lys Ala Gly Val Gly Ile Lys Cys Cys Ser Thr Asp Asn Cys Asn
    50                  55                  60

Leu Phe Lys Phe Gly Lys Pro Arg
65                  70


<210> SEQ ID NO 45
<211> LENGTH: 73
<212> TYPE: PRT
<213> ORGANISM: Acanthophis antarcticus

<400> SEQUENCE: 45

Val Ile Cys Tyr Arg Gly Tyr Asn Asn Pro Gln Thr Cys Pro Pro Gly
 1               5                  10                  15

Glu Asn Val Cys Phe Thr Arg Thr Trp Cys Asp Ala Phe Cys Ser Ser
            20                  25                  30

Arg Gly Lys Val Val Glu Leu Gly Cys Ala Ala Thr Cys Pro Ile Val
        35                  40                  45

Lys Ser Tyr Asn Glu Val Lys Cys Cys Ser Thr Asp Lys Cys Asn Pro
    50                  55                  60

Phe Pro Val Arg Pro Arg Arg Pro Pro
65                  70


<210> SEQ ID NO 46
<211> LENGTH: 74
<212> TYPE: PRT
<213> ORGANISM: Acanthophis antarcticus

<400> SEQUENCE: 46

Val Ile Cys Tyr Arg Lys Tyr Thr Asn Asn Val Lys Thr Cys Pro Asp
 1               5                  10                  15

Gly Glu Asn Val Cys Tyr Thr Lys Met Trp Cys Asp Gly Phe Cys Thr
            20                  25                  30

Ser Arg Gly Lys Val Val Glu Leu Gly Cys Ala Ala Thr Cys Pro Ile
        35                  40                  45

Arg Lys Pro Gly Asn Glu Val Lys Cys Cys Ser Thr Asn Lys Cys Asn
    50                  55                  60
```

His Pro Pro Lys Arg Lys Lys Arg Arg Pro
65 70

<210> SEQ ID NO 47
<211> LENGTH: 68
<212> TYPE: PRT
<213> ORGANISM: Aspidelaps scutatus

<400> SEQUENCE: 47

Arg Ile Cys Tyr Ile Ala Pro Tyr Asp His Lys Thr Cys Ala Ala Gly
1 5 10 15

Glu Asn Ile Cys Tyr Leu Lys Ala Trp Cys Asp Ala Trp Cys Ser Ser
20 25 30

Arg Gly Lys Lys Leu Glu Phe Gly Cys Ala Ala Thr Cys Pro Thr Val
35 40 45

Lys Pro Gly Val Asp Ile Ser Cys Cys Asp Thr Asp Asn Cys Asn Pro
50 55 60

His Pro Lys Leu
65

<210> SEQ ID NO 48
<211> LENGTH: 70
<212> TYPE: PRT
<213> ORGANISM: Astrotia stokesii

<400> SEQUENCE: 48

Leu Ser Cys Tyr Leu Gly Tyr Lys His Ser Gln Thr Cys Pro Pro Gly
1 5 10 15

Glu Asn Val Cys Phe Val Lys Thr Trp Cys Asp Gly Phe Cys Asn Thr
20 25 30

Arg Gly Glu Arg Ile Ile Met Gly Cys Ala Ala Thr Cys Pro Thr Ala
35 40 45

Lys Ser Gly Val His Ile Ala Cys Cys Ser Thr Asp Asn Cys Asn Ile
50 55 60

Tyr Ala Lys Trp Gly Ser
65 70

<210> SEQ ID NO 49
<211> LENGTH: 72
<212> TYPE: PRT
<213> ORGANISM: Astrotia stokesii

<400> SEQUENCE: 49

Leu Ser Cys Tyr Leu Gly Tyr Lys His Ser Gln Thr Cys Pro Pro Gly
1 5 10 15

Glu Asn Val Cys Phe Val Lys Thr Trp Cys Asp Ala Phe Cys Ser Thr
20 25 30

Arg Gly Glu Arg Ile Val Met Gly Cys Ala Ala Thr Cys Pro Thr Ala
35 40 45

Lys Ser Gly Val His Ile Ala Cys Cys Ser Thr Asp Asn Cys Asn Ile
50 55 60

Tyr Thr Lys Trp Gly Ser Gly Arg
65 70

<210> SEQ ID NO 50
<211> LENGTH: 71
<212> TYPE: PRT
<213> ORGANISM: Austrelaps superbus

<400> SEQUENCE: 50

Leu Ile Cys Tyr Val Asp Ser Lys Thr Ser Arg Thr Cys Pro Pro Gly
1 5 10 15

Glu Asn Val Cys Phe Thr Glu Thr Trp Cys Asp Ala Arg Cys Ser Leu
20 25 30

Leu Gly Lys Arg Val Asp Leu Gly Cys Ala Ala Thr Cys Pro Thr Ala
35 40 45

Lys Pro Gly Val Asp Ile Thr Cys Cys Ser Thr Asp Lys Cys Asn Pro
50 55 60

Phe Pro Thr Gln Lys His Arg
65 70

<210> SEQ ID NO 51
<211> LENGTH: 69
<212> TYPE: PRT
<213> ORGANISM: Austrelaps superbus

<400> SEQUENCE: 51

Phe Ser Cys Tyr Lys Thr Pro Asp Val Lys Ser Glu Pro Cys Ala Pro
1 5 10 15

Gly Glu Asn Leu Cys Tyr Thr Lys Thr Trp Cys Asp Arg Phe Cys Ser
20 25 30

Ile Arg Gly Lys Val Ile Glu Leu Gly Cys Ala Ala Thr Cys Pro Pro
35 40 45

Ala Glu Pro Arg Lys Asp Ile Thr Cys Cys Ser Thr Asp Asn Cys Asn
50 55 60

Pro His Pro Ala His
65

<210> SEQ ID NO 52
<211> LENGTH: 73
<212> TYPE: PRT
<213> ORGANISM: Bungarus candidus

<400> SEQUENCE: 52

Leu Leu Cys Tyr Lys Thr Pro Ser Pro Ile Asn Ala Glu Thr Cys Pro
1 5 10 15

Pro Gly Glu Asn Leu Cys Tyr Thr Lys Met Trp Cys Asp Ala Trp Cys
20 25 30

Ser Ser Arg Gly Lys Val Val Glu Leu Gly Cys Ala Ala Thr Cys Pro
35 40 45

Ser Lys Lys Pro Tyr Glu Glu Val Thr Cys Cys Ser Thr Asp Lys Cys
50 55 60

Asn Pro His Pro Lys Gln Arg Pro Asp
65 70

<210> SEQ ID NO 53
<211> LENGTH: 73
<212> TYPE: PRT
<213> ORGANISM: Bungarus candidus

<400> SEQUENCE: 53

Leu Leu Cys Tyr Lys Thr Pro Ser Pro Ile Asn Ala Glu Thr Cys Pro
1 5 10 15

Pro Gly Glu Asn Leu Cys Tyr Thr Lys Met Trp Cys Asp Ala Trp Cys
20 25 30

Ser Ser Arg Gly Lys Val Ile Glu Leu Gly Cys Ala Ala Thr Cys Pro
35 40 45

-continued

```
Ser Lys Lys Pro Tyr Glu Glu Val Thr Cys Cys Ser Thr Asp Lys Cys
    50                  55                  60

Asn Pro His Pro Lys Gln Arg Pro Gly
65                  70
```

<210> SEQ ID NO 54
<211> LENGTH: 73
<212> TYPE: PRT
<213> ORGANISM: Bungarus candidus

<400> SEQUENCE: 54

```
Leu Leu Cys Tyr Lys Thr Pro Ile Pro Ile Asn Ala Glu Thr Cys Pro
 1               5                  10                  15

Pro Gly Glu Asn Leu Cys Tyr Thr Lys Met Trp Cys Asp Ile Trp Cys
            20                  25                  30

Ser Ser Arg Gly Lys Val Val Glu Leu Gly Cys Ala Ala Thr Cys Pro
        35                  40                  45

Ser Lys Lys Pro Tyr Glu Glu Val Thr Cys Cys Ser Thr Asp Lys Cys
    50                  55                  60

Asn Pro His Pro Lys Gln Arg Pro Asp
65                  70
```

<210> SEQ ID NO 55
<211> LENGTH: 74
<212> TYPE: PRT
<213> ORGANISM: Bungarus candidus

<400> SEQUENCE: 55

```
Ile Val Cys His Thr Thr Ala Thr Ser Pro Ile Ser Ala Val Thr Cys
 1               5                  10                  15

Pro Pro Gly Glu Asn Leu Cys Tyr Arg Lys Met Phe Cys Asp Ala Ile
            20                  25                  30

Cys Ser Ser Arg Gly Lys Val Val Glu Leu Gly Cys Ala Ala Thr Cys
        35                  40                  45

Pro Ser Lys Lys Pro Tyr Glu Glu Val Thr Cys Cys Ser Asn Asp Lys
    50                  55                  60

Cys Asn Pro His Pro Lys Gln Arg Pro Gly
65                  70
```

<210> SEQ ID NO 56
<211> LENGTH: 71
<212> TYPE: PRT
<213> ORGANISM: Boulengerina annulata

<400> SEQUENCE: 56

```
Ile Arg Cys Phe Ile Thr Pro Arg Val Ser Ser Gln Ala Cys Pro Asp
 1               5                  10                  15

Gly His Val Cys Tyr Thr Lys Thr Trp Cys Asp Asn Phe Cys Gly Ile
            20                  25                  30

Asn Gly Lys Arg Val Asp Leu Gly Cys Ala Ala Thr Cys Pro Thr Val
        35                  40                  45

Lys Pro Gly Val Asp Ile Lys Cys Cys Ser Thr Asp Asn Cys Asn Pro
    50                  55                  60

Phe Pro Thr Arg Lys Arg Pro
65                  70
```

<210> SEQ ID NO 57
<211> LENGTH: 66
<212> TYPE: PRT

<213> ORGANISM: Bungarus flaviceps

<400> SEQUENCE: 57

Arg Thr Cys Leu Ile Ser Pro Ser Ser Thr Ser Gln Thr Cys Pro Lys
1 5 10 15

Gly Gln Asp Ile Cys Phe Thr Lys Ala Phe Cys Asp Arg Trp Cys Ser
20 25 30

Ser Arg Gly Pro Val Ile Glu Gln Gly Cys Ala Ala Thr Cys Pro Glu
35 40 45

Phe Thr Ser Arg Tyr Lys Ser Leu Leu Cys Cys Thr Thr Asp Asn Cys
50 55 60

Asn His
65

<210> SEQ ID NO 58
<211> LENGTH: 74
<212> TYPE: PRT
<213> ORGANISM: Bungarus multicinctus

<400> SEQUENCE: 58

Ile Val Cys His Thr Thr Ala Thr Ser Pro Ile Ser Ala Val Thr Cys
1 5 10 15

Pro Pro Gly Glu Asn Leu Cys Tyr Arg Lys Met Trp Cys Asp Ala Phe
20 25 30

Cys Ser Ser Lys Gly Lys Val Val Glu Leu Gly Cys Ala Ala Thr Cys
35 40 45

Pro Ser Lys Lys Pro Tyr Glu Glu Val Thr Cys Cys Ser Thr Asp Lys
50 55 60

Cys Asn Pro His Pro Lys Gln Arg Pro Gly
65 70

<210> SEQ ID NO 59
<211> LENGTH: 74
<212> TYPE: PRT
<213> ORGANISM: Bungarus multicinctus

<400> SEQUENCE: 59

Ile Val Cys His Thr Thr Ala Thr Ser Pro Ile Ser Ala Val Thr Cys
1 5 10 15

Pro Pro Gly Glu Asn Leu Cys Tyr Arg Lys Met Trp Cys Asp Ala Phe
20 25 30

Cys Ser Ser Arg Gly Lys Val Val Glu Leu Gly Cys Ala Ala Thr Cys
35 40 45

Pro Ser Lys Lys Pro Tyr Glu Glu Val Thr Cys Cys Ser Thr Asp Lys
50 55 60

Cys Asn Pro His Pro Lys Gln Arg Pro Gly
65 70

<210> SEQ ID NO 60
<211> LENGTH: 74
<212> TYPE: PRT
<213> ORGANISM: Bungarus multicinctus

<400> SEQUENCE: 60

Ile Val Cys His Thr Thr Ala Thr Ser Pro Ile Ser Ala Val Thr Cys
1 5 10 15

Pro Pro Gly Glu Asn Leu Cys Tyr Arg Lys Met Trp Cys Asp Ala Phe
20 25 30

```
Cys Ser Ser Arg Gly Lys Val Val Glu Leu Gly Cys Ala Ala Thr Cys
        35                  40                  45

Pro Ser Lys Lys Pro Tyr Glu Glu Val Thr Cys Cys Ser Thr Asp Gln
    50                  55                  60

Cys His Pro His Pro Lys Gln Arg Pro Gly
65                  70
```

<210> SEQ ID NO 61
<211> LENGTH: 74
<212> TYPE: PRT
<213> ORGANISM: Bungarus multicinctus

<400> SEQUENCE: 61

```
Ile Val Cys His Thr Thr Ala Thr Ser Pro Ile Ser Ala Val Thr Cys
 1               5                  10                  15

Pro Pro Gly Glu Asn Leu Cys Tyr Arg Lys Met Trp Cys Asp Val Phe
            20                  25                  30

Cys Ser Ser Arg Gly Lys Val Val Glu Leu Gly Cys Ala Ala Thr Cys
        35                  40                  45

Pro Ser Lys Lys Pro Tyr Glu Glu Val Thr Cys Cys Ser Thr Asp Lys
    50                  55                  60

Cys Asn Pro His Pro Lys Gln Arg Pro Gly
65                  70
```

<210> SEQ ID NO 62
<211> LENGTH: 67
<212> TYPE: PRT
<213> ORGANISM: Demansia vestigiata

<400> SEQUENCE: 62

```
Arg Thr Cys Leu Lys Thr Pro Glu Val Lys Ser Glu Pro Cys Pro Pro
 1               5                  10                  15

Gly Gln Glu Val Cys Tyr Thr Lys Ala Trp Cys Asp Arg Met Cys Ser
            20                  25                  30

Phe Arg Gly Lys Val Ile Glu Leu Gly Cys Ala Ala Thr Cys Pro Arg
        35                  40                  45

Gln Glu Pro Gly Lys Glu Ile Thr Cys Cys Ser Thr Asp Asp Cys Asn
    50                  55                  60

Thr His Pro
65
```

<210> SEQ ID NO 63
<211> LENGTH: 67
<212> TYPE: PRT
<213> ORGANISM: Demansia vestigiata

<400> SEQUENCE: 63

```
Arg Thr Cys Leu Lys Thr Pro Glu Val Lys Ser Glu Pro Cys Pro Pro
 1               5                  10                  15

Gly Gln Glu Val Cys Tyr Thr Lys Ala Trp Arg Asp Arg Met Cys Ser
            20                  25                  30

Phe Arg Gly Lys Val Ile Glu Leu Gly Cys Ala Ala Thr Cys Pro Arg
        35                  40                  45

Gln Glu Pro Gly Lys Glu Ile Thr Cys Cys Ser Thr Asp Asp Cys Asn
    50                  55                  60

Thr His Pro
65
```

-continued

<210> SEQ ID NO 64
<211> LENGTH: 67
<212> TYPE: PRT
<213> ORGANISM: Laticauda laticaudata

<400> SEQUENCE: 64

```
Arg Ile Cys Phe Lys Thr Pro Tyr Val Lys Ser Glu Thr Cys Pro Pro
 1               5                  10                  15

Gly Gln Glu Leu Cys Tyr Thr Lys Thr Trp Cys Asp Arg Phe Cys Ser
            20                  25                  30

Ile Arg Gly Lys Val Ile Glu Leu Gly Cys Thr Ala Thr Cys Pro Arg
        35                  40                  45

Ala Glu Pro Lys Glu Asp Thr Thr Cys Cys Ser Lys Asp Asn Cys Asn
    50                  55                  60

Pro His Pro
65
```

<210> SEQ ID NO 65
<211> LENGTH: 69
<212> TYPE: PRT
<213> ORGANISM: Laticauda colubrina

<400> SEQUENCE: 65

```
Arg Ile Cys Tyr Leu Ala Pro Arg Asp Thr Gln Ile Cys Ala Pro Gly
 1               5                  10                  15

Gln Glu Ile Cys Tyr Leu Lys Ser Trp Asp Asp Gly Thr Gly Ser Ile
            20                  25                  30

Arg Gly Asn Arg Leu Glu Phe Gly Cys Ala Ala Thr Cys Pro Thr Val
        35                  40                  45

Lys Arg Gly Ile His Ile Lys Cys Cys Ser Thr Asp Lys Cys Asn Pro
    50                  55                  60

His Pro Lys Leu Ala
65
```

<210> SEQ ID NO 66
<211> LENGTH: 69
<212> TYPE: PRT
<213> ORGANISM: Laticauda colubrina

<400> SEQUENCE: 66

```
Arg Ile Cys Tyr Leu Ala Pro Arg Asp Thr Gln Ile Cys Ala Pro Gly
 1               5                  10                  15

Gln Glu Ile Cys Tyr Leu Lys Ser Trp Asp Asp Gly Thr Gly Phe Leu
            20                  25                  30

Lys Gly Asn Arg Leu Glu Phe Gly Cys Ala Ala Thr Cys Pro Thr Val
        35                  40                  45

Lys Pro Gly Ile Asp Ile Lys Cys Cys Ser Thr Asp Lys Cys Asn Pro
    50                  55                  60

His Pro Lys Leu Ala
65
```

<210> SEQ ID NO 67
<211> LENGTH: 71
<212> TYPE: PRT
<213> ORGANISM: Lapemis hardwickii

<400> SEQUENCE: 67

```
Leu Ser Cys Tyr Leu Gly Tyr Lys Arg Ser Gln Thr Cys Pro Pro Gly
 1               5                  10                  15
```

```
Glu Lys Val Cys Phe Val Lys Ser Trp Cys Asp Ala Phe Cys Gly Ser
            20                  25                  30

Arg Gly Lys Arg Ile Glu Met Gly Cys Ala Ala Thr Cys Pro Thr Val
        35                  40                  45

Lys Asp Gly Ile Asp Ile Thr Cys Cys Ala Thr Asp Asn Cys Asn Thr
    50                  55                  60

Tyr Ala Asn Trp Gly Ser Gly
65                  70


<210> SEQ ID NO 68
<211> LENGTH: 72
<212> TYPE: PRT
<213> ORGANISM: Lapemis hardwickii

<400> SEQUENCE: 68

Arg Thr Cys Tyr Arg Thr His Pro Tyr Lys Pro Glu Thr Cys Pro Pro
 1               5                  10                  15

Gly Gln Asn Leu Cys Tyr Lys Lys Ser Trp Cys Asp Ala Phe Cys Ser
            20                  25                  30

Ser Arg Gly Lys Val Ile Glu Leu Gly Cys Thr Ala Lys Cys Pro Thr
        35                  40                  45

Val Lys His Gly Lys Asp Ile Asn Cys Cys Ala Thr Asp Asn Cys Asn
    50                  55                  60

Thr Val Ala Asn Trp Lys Ser Arg
65                  70


<210> SEQ ID NO 69
<211> LENGTH: 66
<212> TYPE: PRT
<213> ORGANISM: Laticauda semifasciata

<400> SEQUENCE: 69

Arg Glu Cys Tyr Leu Asn Pro His Asp Thr Gln Thr Cys Pro Ser Gly
 1               5                  10                  15

Gln Glu Ile Cys Tyr Val Lys Ser Trp Cys Asn Ala Trp Cys Ser Ser
            20                  25                  30

Arg Gly Lys Val Leu Glu Phe Gly Cys Ala Ala Thr Cys Pro Ser Val
        35                  40                  45

Asn Thr Gly Thr Glu Ile Lys Cys Cys Ser Ala Asp Lys Cys Asn Thr
    50                  55                  60

Tyr Pro
65


<210> SEQ ID NO 70
<211> LENGTH: 66
<212> TYPE: PRT
<213> ORGANISM: Laticauda semifasciata

<400> SEQUENCE: 70

Arg Glu Cys Tyr Leu Asn Pro His Asp Thr Gln Thr Cys Pro Ser Gly
 1               5                  10                  15

Gln Glu Ile Cys Tyr Val Lys Ser Trp Cys Asn Ala Trp Cys Ser Ser
            20                  25                  30

Arg Gly Lys Val Leu Glu Phe Gly Cys Ala Ala Thr Cys Pro Ser Val
        35                  40                  45

Asn Thr Gly Thr Glu Ile Lys Cys Cys Ser Ala Asp Lys Cys Asn Thr
    50                  55                  60

Tyr Pro
```

65

<210> SEQ ID NO 71
<211> LENGTH: 73
<212> TYPE: PRT
<213> ORGANISM: Notechis scutatus

<400> SEQUENCE: 71

```
Leu Ile Cys Tyr Met Gly Pro Lys Thr Pro Arg Thr Cys Pro Arg Gly
 1               5                  10                  15

Gln Asn Leu Cys Tyr Thr Lys Thr Trp Cys Asp Ala Phe Cys Ser Ser
            20                  25                  30

Arg Gly Lys Val Val Glu Leu Gly Cys Ala Ala Thr Cys Pro Ile Ala
        35                  40                  45

Lys Ser Tyr Glu Asp Val Thr Cys Cys Ser Thr Asp Asn Cys Asn Pro
    50                  55                  60

Phe Pro Val Arg Pro Arg His Pro Pro
65                  70
```

<210> SEQ ID NO 72
<211> LENGTH: 71
<212> TYPE: PRT
<213> ORGANISM: Oxyuranus scutellatus

<400> SEQUENCE: 72

```
Arg Arg Cys Phe Thr Thr Pro Ser Val Arg Ser Glu Arg Cys Pro Pro
 1               5                  10                  15

Gly Gln Glu Val Cys Tyr Thr Lys Thr Trp Thr Asp Gly His Gly Gly
            20                  25                  30

Ser Arg Gly Lys Arg Val Asp Leu Gly Cys Ala Ala Thr Cys Pro Thr
        35                  40                  45

Pro Lys Lys Lys Asp Ile Lys Ile Ile Cys Cys Ser Thr Asp Asn Cys
    50                  55                  60

Asn Thr Phe Pro Lys Trp Pro
65                  70
```

<210> SEQ ID NO 73
<211> LENGTH: 71
<212> TYPE: PRT
<213> ORGANISM: Oxyuranus microlepidotus

<400> SEQUENCE: 73

```
Arg Arg Cys Phe Ile Thr Pro Asp Val Arg Ser Glu Arg Cys Pro Pro
 1               5                  10                  15

Gly Gln Glu Val Cys Tyr Thr Lys Thr Trp Cys Asp Gly Phe Cys Ser
            20                  25                  30

Ser Arg Gly Lys Arg Val Asp Leu Gly Cys Ala Ala Thr Cys Pro Thr
        35                  40                  45

Pro Lys Lys Lys Gly Ile Asp Ile Ile Cys Cys Ser Lys Asp Asn Cys
    50                  55                  60

Asn Thr Phe Pro Lys Trp Pro
65                  70
```

<210> SEQ ID NO 74
<211> LENGTH: 71
<212> TYPE: PRT
<213> ORGANISM: Oxyuranus microlepidotus

<400> SEQUENCE: 74

Arg Arg Cys Phe Ile Thr Pro Asp Val Arg Ser Glu Arg Cys Pro Pro
1 5 10 15

Gly Gln Glu Val Cys Tyr Thr Lys Thr Trp Cys Asp Gly Phe Cys Gly
20 25 30

Ser Arg Gly Lys Arg Val Asp Leu Gly Cys Ala Ala Thr Cys Pro Thr
35 40 45

Pro Lys Lys Lys Gly Ile Asp Ile Ile Cys Cys Ser Lys Asp Asn Cys
50 55 60

Asn Thr Phe Pro Lys Trp Pro
65 70

<210> SEQ ID NO 75
<211> LENGTH: 71
<212> TYPE: PRT
<213> ORGANISM: Oxyuranus microlepidotus

<400> SEQUENCE: 75

Arg Arg Cys Phe Thr Thr Pro Ser Val Arg Ser Glu Arg Cys Pro Pro
1 5 10 15

Gly Gln Glu Val Cys Tyr Thr Lys Thr Trp Thr Asp Gly His Gly Gly
20 25 30

Ser Arg Gly Lys Arg Val Asp Leu Gly Cys Ala Ala Thr Cys Pro Thr
35 40 45

Pro Lys Lys Lys Asp Ile Lys Thr Ile Cys Cys Ser Lys Asp Asn Cys
50 55 60

Asn Thr Phe Pro Lys Trp Pro
65 70

<210> SEQ ID NO 76
<211> LENGTH: 71
<212> TYPE: PRT
<213> ORGANISM: Oxyuranus microlepidotus

<400> SEQUENCE: 76

Arg Arg Cys Phe Ile Thr Pro Asp Val Arg Ser Glu Arg Cys Pro Pro
1 5 10 15

Gly Gln Glu Val Cys Tyr Thr Lys Thr Trp Cys Asp Gly Phe Cys Gly
20 25 30

Ser Arg Gly Lys Arg Val Asp Leu Gly Cys Ala Ala Thr Cys Pro Thr
35 40 45

Pro Lys Lys Lys Asp Ile Lys Ile Ile Cys Cys Ser Lys Asp Asn Cys
50 55 60

Asn Thr Phe Pro Lys Trp Pro
65 70

<210> SEQ ID NO 77
<211> LENGTH: 68
<212> TYPE: PRT
<213> ORGANISM: Pseudechis australis

<400> SEQUENCE: 77

Leu Thr Cys Tyr Lys Gly Arg Asp Arg Ser Ser Glu Thr Cys Arg Ser
1 5 10 15

Glu Gln Glu Leu Cys Cys Thr Lys Thr Trp Cys Asp Gln Trp Cys Gln
20 25 30

Asp Arg Gly Pro Arg Leu Glu Met Gly Cys Thr Ala Thr Cys Pro Arg
35 40 45

Arg Met Pro Gly Leu Asp Phe Thr Cys Cys Thr Thr Asp Asn Cys Asn

```
    50                  55                  60

Pro Val Pro Thr
65


<210> SEQ ID NO 78
<211> LENGTH: 68
<212> TYPE: PRT
<213> ORGANISM: Pseudechis australis

<400> SEQUENCE: 78

Leu Thr Cys Tyr Lys Gly Arg Asp Arg Ser Ser Glu Thr Cys Arg Ser
 1               5                  10                  15

Glu Gln Glu Leu Cys Cys Thr Lys Thr Trp Cys Asp Gln Trp Cys Gln
            20                  25                  30

Asp Arg Gly Pro Arg Leu Glu Met Gly Cys Thr Ala Thr Cys Pro Arg
        35                  40                  45

Arg Met Pro Gly Leu Asp Phe Thr Cys Cys Thr Thr Asp Asn Cys Asn
    50                  55                  60

Pro Val Pro Thr
65


<210> SEQ ID NO 79
<211> LENGTH: 72
<212> TYPE: PRT
<213> ORGANISM: Tropidechis carinatus

<400> SEQUENCE: 79

Phe Ser Cys Tyr Lys Thr Pro His Val Lys Ser Glu Pro Cys Ala Pro
 1               5                  10                  15

Gly Gln Asn Leu Cys Tyr Thr Lys Thr Trp Cys Asp Ala Phe Cys Phe
            20                  25                  30

Ser Arg Gly Arg Val Ile Glu Leu Gly Cys Ala Ala Thr Cys Pro Pro
        35                  40                  45

Ala Glu Pro Lys Lys Asp Ile Ser Cys Cys Ser Thr Asp Asn Cys Asn
    50                  55                  60

Pro His Pro Ala His Gln Ser Arg
65                  70


<210> SEQ ID NO 80
<211> LENGTH: 62
<212> TYPE: PRT
<213> ORGANISM: Naja kaouthia

<400> SEQUENCE: 80

Leu Glu Cys His Asn Gln Gln Ser Ser Gln Thr Pro Thr Thr Thr Gly
 1               5                  10                  15

Cys Ser Gly Gly Glu Thr Asn Cys Tyr Lys Lys Arg Trp Arg Asp His
            20                  25                  30

Arg Gly Tyr Arg Thr Glu Arg Gly Cys Gly Cys Pro Ser Val Arg Asn
        35                  40                  45

Gly Ile Glu Ile Asn Cys Cys Thr Thr Asp Arg Cys Asn Asn
    50                  55                  60


<210> SEQ ID NO 81
<211> LENGTH: 62
<212> TYPE: PRT
<213> ORGANISM: Naja kaouthia

<400> SEQUENCE: 81
```

```
Leu Glu Cys His Asn Gln Gln Ser Ser Gln Ala Pro Thr Thr Lys Thr
 1               5                  10                  15

Cys Ser Gly Gly Glu Thr Asn Cys Tyr Lys Lys Arg Trp Arg Asp His
            20                  25                  30

Arg Gly Tyr Arg Thr Glu Arg Gly Cys Gly Cys Pro Ser Val Arg Asn
        35                  40                  45

Gly Ile Glu Ile Asn Cys Cys Thr Thr Asp Arg Cys Asn Asn
    50                  55                  60


<210> SEQ ID NO 82
<211> LENGTH: 61
<212> TYPE: PRT
<213> ORGANISM: Naja kaouthia

<400> SEQUENCE: 82

Leu Glu Cys His Asn Gln Gln Ser Ser Gln Ala Pro Thr Thr Lys Thr
 1               5                  10                  15

Cys Ser Gly Glu Thr Asn Cys Tyr Lys Lys Trp Trp Ser Asp His Arg
            20                  25                  30

Gly Thr Ile Ile Glu Arg Gly Cys Gly Cys Pro Lys Val Lys Pro Gly
        35                  40                  45

Val Asn Leu Asn Cys Cys Arg Thr Asp Arg Cys Asn Asn
    50                  55                  60


<210> SEQ ID NO 83
<211> LENGTH: 61
<212> TYPE: PRT
<213> ORGANISM: Naja kaouthia

<400> SEQUENCE: 83

Leu Glu Cys His Asn Gln Gln Ser Ser Gln Thr Pro Thr Thr Lys Thr
 1               5                  10                  15

Cys Ser Gly Glu Thr Asn Cys Tyr Lys Lys Trp Trp Ser Asp His Arg
            20                  25                  30

Gly Thr Ile Ile Glu Arg Gly Cys Gly Cys Pro Lys Val Lys Pro Gly
        35                  40                  45

Val Asn Leu Asn Cys Cys Arg Arg Asp Arg Cys Asn Asn
    50                  55                  60


<210> SEQ ID NO 84
<211> LENGTH: 61
<212> TYPE: PRT
<213> ORGANISM: Naja oxiana

<400> SEQUENCE: 84

Leu Glu Cys His Asn Gln Gln Ser Ser Gln Pro Pro Thr Thr Lys Thr
 1               5                  10                  15

Cys Ser Gly Glu Thr Asn Cys Tyr Lys Lys Trp Trp Ser Asp His Arg
            20                  25                  30

Gly Thr Ile Ile Glu Arg Gly Cys Gly Cys Pro Lys Val Lys Pro Gly
        35                  40                  45

Val Asn Leu Asn Cys Cys Arg Thr Asp Arg Cys Asn Asn
    50                  55                  60


<210> SEQ ID NO 85
<211> LENGTH: 60
<212> TYPE: PRT
<213> ORGANISM: Micrurus nigrocinctus

<400> SEQUENCE: 85
```

Met Ile Cys His Asn Gln Gln Ser Ser Gln Pro Pro Thr Ile Lys Thr
1 5 10 15

Cys Ser Glu Gly Gln Cys Tyr Lys Lys Thr Trp Arg Asp His Arg Gly
20 25 30

Thr Ile Ser Glu Arg Gly Cys Gly Cys Pro Thr Val Lys Pro Gly Ile
35 40 45

His Ile Ser Cys Cys Ala Ser Asp Lys Cys Asn Ala
50 55 60

<210> SEQ ID NO 86
<211> LENGTH: 58
<212> TYPE: PRT
<213> ORGANISM: Pseudonaja textilis

<400> SEQUENCE: 86

Leu Thr Cys Tyr Lys Ser Leu Ser Gly Thr Val Val Cys Lys Pro His
1 5 10 15

Glu Thr Ile Cys Tyr Arg Arg Leu Ile Pro Ala Thr His Gly Asn Ala
20 25 30

Ile Ile Asp Arg Gly Cys Ser Thr Ser Cys Pro Gly Gly Asn Arg Pro
35 40 45

Val Cys Cys Ser Thr Asp Leu Cys Asn Lys
50 55

<210> SEQ ID NO 87
<211> LENGTH: 58
<212> TYPE: PRT
<213> ORGANISM: Pseudonaja textilis

<400> SEQUENCE: 87

Leu Thr Cys Tyr Lys Arg Tyr Phe Asp Thr Val Val Cys Lys Pro Gln
1 5 10 15

Glu Thr Ile Cys Tyr Arg Tyr Ile Ile Pro Ala Thr His Gly Asn Ala
20 25 30

Ile Thr Thr Arg Gly Cys Ser Thr Ser Cys Pro Ser Gly Ile Arg Leu
35 40 45

Val Cys Cys Ser Thr Asp Leu Cys Asn Lys
50 55

<210> SEQ ID NO 88
<211> LENGTH: 58
<212> TYPE: PRT
<213> ORGANISM: Pseudonaja textilis

<400> SEQUENCE: 88

Leu Thr Cys Tyr Lys Gly Tyr His Asp Thr Val Val Cys Lys Pro His
1 5 10 15

Glu Thr Ile Cys Tyr Arg Tyr Leu Val Pro Ala Thr His Gly Asn Ala
20 25 30

Ile Pro Ala Arg Gly Cys Gly Thr Ser Cys Pro Gly Gly Asn His Pro
35 40 45

Val Cys Cys Ser Thr Asp Leu Cys Asn Lys
50 55

<210> SEQ ID NO 89
<211> LENGTH: 61
<212> TYPE: PRT
<213> ORGANISM: Naja pallida

<400> SEQUENCE: 89

Leu Glu Cys His Asn Gln Gln Ser Ser Gln Pro Pro Thr Thr Lys Thr
1 5 10 15

Cys Pro Gly Glu Thr Asn Cys Tyr Lys Lys Val Trp Arg Asp His Arg
20 25 30

Gly Thr Ile Ile Glu Arg Gly Cys Gly Cys Pro Thr Val Lys Pro Gly
35 40 45

Ile Lys Leu Asn Cys Cys Thr Thr Asp Lys Cys Asn Asn
50 55 60

<210> SEQ ID NO 90
<211> LENGTH: 61
<212> TYPE: PRT
<213> ORGANISM: Naja haje anulifera

<400> SEQUENCE: 90

Leu Glu Cys His Asn Gln Gln Ser Ser Gln Pro Pro Thr Thr Lys Thr
1 5 10 15

Cys Pro Gly Glu Thr Asn Cys Tyr Lys Lys Arg Trp Arg Asp His Arg
20 25 30

Gly Ser Ile Thr Glu Arg Gly Cys Gly Cys Pro Ser Val Lys Lys Gly
35 40 45

Ile Glu Ile Asn Cys Cys Thr Thr Asp Lys Cys Asn Asn
50 55 60

<210> SEQ ID NO 91
<211> LENGTH: 60
<212> TYPE: PRT
<213> ORGANISM: Acalyptophis peroni

<400> SEQUENCE: 91

Met Thr Cys Cys Asn Gln Gln Ser Ser Gln Pro Lys Thr Thr Thr Asn
1 5 10 15

Cys Ala Gly Asn Ser Cys Tyr Lys Lys Thr Trp Ser Asp His Arg Gly
20 25 30

Thr Ile Ile Glu Arg Gly Cys Gly Cys Pro Gln Val Lys Ser Gly Ile
35 40 45

Lys Leu Glu Cys Cys His Thr Asn Glu Cys Asn Asn
50 55 60

<210> SEQ ID NO 92
<211> LENGTH: 60
<212> TYPE: PRT
<213> ORGANISM: Dendroaspis polylepis

<400> SEQUENCE: 92

Arg Ile Cys Tyr Asn His Gln Ser Thr Thr Arg Ala Thr Thr Lys Ser
1 5 10 15

Cys Glu Glu Asn Ser Cys Tyr Lys Lys Tyr Trp Arg Asp His Arg Gly
20 25 30

Thr Ile Ile Glu Arg Gly Cys Gly Cys Pro Lys Val Lys Pro Gly Val
35 40 45

Gly Ile His Cys Cys Gln Ser Asp Lys Cys Asn Tyr
50 55 60

<210> SEQ ID NO 93
<211> LENGTH: 62
<212> TYPE: PRT
<213> ORGANISM: Pseudechis australis

<400> SEQUENCE: 93

Met Thr Cys Cys Asn Gln Gln Ser Ser Gln Pro Lys Thr Thr Thr Ile
1 5 10 15

Cys Ala Gly Gly Glu Ser Ser Cys Tyr Lys Lys Thr Trp Ser Asp His
20 25 30

Arg Gly Ser Arg Thr Glu Arg Gly Cys Gly Cys Pro His Val Lys Pro
35 40 45

Gly Ile Lys Leu Thr Cys Cys Lys Thr Asp Glu Cys Asn Asn
50 55 60

<210> SEQ ID NO 94
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 94

Ala Cys Ser Ser Ser Pro Ser Lys His Cys Gly
1 5 10

<210> SEQ ID NO 95
<211> LENGTH: 21
<212> TYPE: DNA
<213> ORGANISM: Artificial Sequence
<220> FEATURE:
<223> OTHER INFORMATION: Oligonucleotide

<400> SEQUENCE: 95
atgaaaactc tgctgctgac c 21

<210> SEQ ID NO 96
<211> LENGTH: 21
<212> TYPE: DNA
<213> ORGANISM: Artificial Sequence
<220> FEATURE:
<223> OTHER INFORMATION: Oligonucleotide

<400> SEQUENCE: 96
ctcaaactac agaactagca g 21

<210> SEQ ID NO 97
<211> LENGTH: 20
<212> TYPE: DNA
<213> ORGANISM: Artificial Sequence
<220> FEATURE:
<223> OTHER INFORMATION: Oligonucleotide

<400> SEQUENCE: 97
gacttaggat acaccataag 20

<210> SEQ ID NO 98
<211> LENGTH: 22
<212> TYPE: DNA
<213> ORGANISM: Artificial Sequence
<220> FEATURE:
<223> OTHER INFORMATION: Oligonucleotide

<400> SEQUENCE: 98
ttgagttttg ctctcatcca tc 22